US007585627B2

(12) United States Patent
Caron et al.

(10) Patent No.: US 7,585,627 B2
(45) Date of Patent: *Sep. 8, 2009

(54) POLYMORPHISM IN TRYPTOPHAN HYDROXYLASE-2 CONTROLS BRAIN SEROTONIN SYNTHESIS

(75) Inventors: Marc G. Caron, Hillsborough, NC (US); Xiaodong Zhang, Durham, NC (US); Martin Beaulieu, Durham, NC (US); Raul R. Gainetdinov, Chapel Hill, NC (US); Tatiana D. Sotnikova, Chapel Hill, NC (US); Ranga R. Krishnan, Chapel Hill, NC (US); David A. Schwartz, Hillsborough, NC (US); Lauranell Burch, Durham, NC (US); Redford B. Williams, Hillsborough, NC (US)

(73) Assignee: Duke University, Durham, NC (US)

( * ) Notice: Subject to any disclaimer, the term of this patent is extended or adjusted under 35 U.S.C. 154(b) by 42 days.

This patent is subject to a terminal disclaimer.

(21) Appl. No.: 11/133,949

(22) Filed: May 20, 2005

(65) Prior Publication Data

US 2006/0029951 A1 Feb. 9, 2006

Related U.S. Application Data

(60) Provisional application No. 60/642,869, filed on Jan. 11, 2005, provisional application No. 60/642,800, filed on Jan. 11, 2005, provisional application No. 60/629,951, filed on Nov. 22, 2004, provisional application No. 60/606,811, filed on Sep. 2, 2004, provisional application No. 60/573,265, filed on May 21, 2004.

(51) Int. Cl.
C12Q 1/68 (2006.01)
G01N 33/567 (2006.01)
C12P 19/34 (2006.01)

(52) U.S. Cl. .......................... 435/6; 435/7.21; 435/91.2
(58) Field of Classification Search ...................... None
See application file for complete search history.

(56) References Cited

U.S. PATENT DOCUMENTS

| | | | |
|---|---|---|---|
| 4,920,122 A | 4/1990 | Naruse et al. | |
| 5,595,772 A | 1/1997 | Wurtman et al. | 462/2 |
| 5,958,429 A | 9/1999 | Wong | 424/400 |
| 6,011,054 A | 1/2000 | Oxenkrug et al. | 514/415 |
| 6,013,622 A | 1/2000 | Bruno et al. | 514/2 |
| 6,191,133 B1 | 2/2001 | Coppen | |
| 6,211,171 B1 | 4/2001 | Sawynok et al. | 514/211.13 |
| 6,218,395 B1 | 4/2001 | Swartz | 514/252.15 |
| 6,239,162 B1 | 5/2001 | Oxenkrug | 514/415 |
| 6,358,944 B1 | 3/2002 | Lederman et al. | 514/220 |
| 6,368,814 B1 | 4/2002 | Ghoshal et al. | 435/7.93 |
| 6,369,051 B1 | 4/2002 | Jenkins | 514/217.08 |
| 6,387,907 B1 | 5/2002 | Hendricks et al. | 514/254.06 |
| 6,387,936 B1 | 5/2002 | Blanchard-Bregeon et al. | 514/367 |
| 6,387,956 B1 | 5/2002 | Shapira et al. | 514/646 |
| 6,472,423 B1 | 10/2002 | Ross et al. | 514/456 |
| 6,492,366 B1 | 12/2002 | Lavielle et al. | 514/248 |
| 6,500,829 B1 | 12/2002 | Wood et al. | 514/249 |
| 6,552,014 B2 | 4/2003 | Serebruany et al. | 514/214.02 |
| 6,579,899 B1 | 6/2003 | Wurtman et al. | |
| 6,656,172 B1 | 12/2003 | Hildebrand | 604/891.1 |
| 6,673,381 B2 | 1/2004 | Bailey et al. | 426/72 |
| 6,808,725 B2 | 10/2004 | Bailey et al. | 426/72 |
| 2006/0142375 A1 | 6/2006 | Krishnan et al. | |

OTHER PUBLICATIONS

Zhang et al, Neuron, 45(1):11-16, Jan. 6, 2005.*
Garriock et al. Lack of association of TPH2 exon XI polymorphisms with major depression and treatment resistance. Molecular Psychiatry 10: 976-977. Jul. 12, 2005.*
Correspondence from Blakely; Zhou et al; Bogaert et al; Glatt et al. and Zhang et al. Neuron 48: 701-706, Dec. 8, 2005.*
Delorme et al. No human tryptophan hydroxylase-2 gene R441H mutation in a large cohort of psychiatric patients ans control subjects. Biological Psychiatry 60: 202-203. (2006).*
Sacco et al. Case-control and family-based association studies of candidate genes in autistic disorder and its endophenotypes: TPH2 and GLO1. BMD Medical Genetics 8(11) 1471-1480. Mar. 8, 2007.*
Sheehan et al. No association between TPH2 gene polymorphisms and ADHD in a UK sample. Neuroscience Letters 412(2): 105-107. Jan. 29, 2007.*
Peters et al. Investigation of serotonin-related genes in antidepressant response. Molecular Psychiatry 9: 879-889. Mar. 30, 2004.*
Zhang et al. Tryptophan Hydroxylase -2 Controls Brin Serotonin Synthesis, Science 305: 217. (2004).*
Erlandsen et al.; "Correction of kinetic and stability defects by tetrahydrobiopterin in phenylketonuria patients with certain phenylalanine hydroxylase mutations" *PNAS* 101:48 16903-16908 (2004).
Sánchez; "R-citalopram attenuates anxiolytic effects of escitalopram in a rat ultrasonic vocalisation model" *European Journal of Pharmacology* 464 155-158 (2003).
Van Pragg; "Serotonin precursors in the treatment of depression" *Adv Biochem Psychopharmacol.* 34 259-286 (1982). Abstract Only.
Zill et al.; "SNP and haplotype analysis of a novel tryptophan hydroxylase isoform (TPH2) gene provide evidence for association with major depression" *Molecular Psychiatry* 1-7 (2004).

(Continued)

*Primary Examiner*—John D. Ulm
*Assistant Examiner*—Stacey MacFarlane
(74) *Attorney, Agent, or Firm*—Myers Bigel Sibley & Sajovec, P.A.

(57) ABSTRACT

A method of screening a subject for a serotonergic neurotransmission dysregulation disorder comprises detecting the presence or absence of an Tph2 mutation in the subject; and then determining that the subject is at increased risk of a serotonergic neurotransmission dysregulation disorder due to the presence or absence of the Tph2 mutation.

4 Claims, 11 Drawing Sheets

OTHER PUBLICATIONS

Zill et al.; "Single Nucleotide Polymorphism and Haplotype Analysis of a Novel Tryptophan Hydroxylase Isoform (TPH2) Gene in Suicide Victims" *Biol Psychiatry* 56 581-586 (2004).
Aghajanian et al.; "Serotonin model of schizophrenia: emerging role of glutamate mechanisms" *Brain Res Brain Res Review* 31 302-312 (2000).
Blier et al.; "Putative mechanisms of action of antidepressant drugs in affective and anxiety disorders and pain" *J Psychiatry Neurosci* 26 37-43 (2001).
Fitzpatrick; "Tetrahydropterin-dependent amino acid hydroxylases" *Annu Rev Biochem* 68 355-381 (1999).
Flattem et al.; "Modified structure of the human serotonin transporter promotor" *Mol Psychiatry* 5 110-115 (2000).
Frazer; "Pharmacology of antidepressants" *J Clin Psychopharmacol* 17:Suppl 1 2S-18S (1997).
Geyer; "Serotonergic functions in arousal and motor activity" *Behav Brain Res* 73 31-35 (1996).
Tamminga; "Serotonin and schizophrenia" *Biol Psychiatry* 44 1079-1080 (1998).
Tecott; "The genes and brains of mice and men" *Am J Psychiatry* 160 646-656 (2003).
Veenstra-VanderWeele et al.; "Pharmacogenetics and the serotonin system: initial studies and future directions" *Eur J Pharmacol* 410 165-181(2000).
Walther et al.; "Synthesis of serotonin by a second tryptophan hydroxylase isoform" *Science* 299 76 (2003).
Walther et al.; "A unique central tryptophan hydroxylase isoform" *Biochem Pharmacol* 66 1673-1680 (2003).
Lucki; "The spectrum of behaviors influenced by serotonin" *Biol Psychiatry* 44 151-162 (1998).
Pey et al.; "Phenylketonuria: genotype-phenotype correlations based on expression analysis of structural and functional mutations in PAH" *Hum Mutat* 21:4 370-378 (2003).
Gainetdinov at al.; "Role of serotonin in the paradoxical calming effect of psychostimulants on hyperactivity" *Science* 283 397-401 (1999).
Bonasera et al.; "Mouse models of serotonin receptor function: toward a genetic dissection of serotonin systems" *Pharmacol Ther* 88 133-142 (2000).
Gingrich et al.; "Dissecting the role of the serotonin system in neurophychiatric disorders using knockout mice" *Psychopharmacology* 155 1-10 (2001).
Murphy et al.; "Experimental gene interaction studies with SERT mutant mice as models for human polygenic and epistatic traits and disorders" *Genes Brain Behav* 2 350-364 (2003).
Lucki et al.; "Sensitivity to the effects of pharmacologically selective antidepressants in different strains of mice" *Psychopharmacology* (Berl) 155 315-322 (2001).
Stenfors et al.; "Pharmacological characterisation of the decrease in 5-HT synthesis in the mouse brain evoked by the selective serotinin re-uptake inhibitor citalopram" *Naunyn Schmiedebergs Arch Pharmacol* 363 222-232 (2001).
Parker et al.; "Assessing the comparative effectiveness of antidepressant therapies: a prospective clinical practice study" *J Clin Psychiatry* 62 117-125 (2001). *Abstract only*.
Martin; "Serotonin syndrome" *Ann Emerg Med* 28 520-526 (1996).
Patel et al.; "Robust and tissue-specific expression of TPH2 versus TPH1 in rat raphe and pineal gland" *Biol Psychiatry* 55 428-433 (2004).
Broquet; "Status of treatment of depression" *South Med J* 92 846-856 (1999).
Zhang X et al. Functional polymorphisms of the brain serotonin synthesizing enzyme tryptophan hydroxylase-2. Cell. Mol. Life Sci. 63:6-11. 2006.
Winge I et al. Characterization of wild-type and mutant forms of human tryptophan hydroxylase 2. Journal of Neurochemistry 100:1648-1657. 2007.
Peters E J et al. *Supplementary Information; Supplementary material files 1-5 (9 pp)*. Investigation of serotonin-related genes in antidepressant response. Molecular Psychiatry 9(9): 879-889. Mar. 30, 2004. www.nature.com/mp/journal/v9/n9/suppinfo/4001502a.html.
Lin Y-M J et al. Association of functional polymorphisms of the human tryptophan hydroxylase 2 gene with risk for bipolar disorder in Han Chinese. Arch Gen Psychiatry. 64(9): 1015-1024. Sep. 2007.
Breidenthal S E et al. Identification of genetic variants in the neuronal form of tryptophan hydroxylase (TPH2). Psychiatric Genetics 14(2): 69-72. 2004.
Gainetdinov R R and Caron M G. Monoamine Transporters: From Genes to Behavior. Annu. Rev. Pharmacol. Toxicol. (2003), vol. 43, pp. 261-284.
Cervo L et al. Geno-type dependent activity of tryptophan hydroxylase-2 determines the response to citalopram in a mouse model of depression. The Journal of Neuroscience (Sep. 7, 2004), vol. 25, No. 36, pp. 8165-8172.
Beaulieu J-M et al. Role of GSK3β in behavioral abnormalities induced by serotonin deficiency. PNAS (Jan. 29, 2008), vol. 105, No. 4, pp. 1333-1338.
Fulmer T. The great (mouse) depression. Science-Business eXchange (Feb. 7, 2008), vol. 1, No. 2, pp. 1, 10-11.
Walther D J et al. Synthesis of serotonin by a second tryptophan hydroxylase isoform. Science (Jan. 3, 2003), vol. 299, p. 76, *Supporting Online Material*, pp. 1-7.
International Search Report and Written Opinion, PCT/US05/17952, mailed Mar. 18, 2008.
Côte F et al. Disruption of the nonneuronal *tph1* gene demonstrates the importance of peripheral serotonin in cardiac function. PNAS USA (Nov. 13, 2003), vol. 100, No. 23, pp. 13525-13530.
De Luca et al. Analysis of the novel TPH2 gene in bipolar disorder and suicidality. Molecular Psychiatry (2004), vol. 9, pp. 896-897.
McKinney J et al. A loss-of-function mutation in tryptophan hydroxylase 2 segregating with attention-deficit/hyperactivity disorder. Molecular Psychiatry (2008), vol. 13, pp. 365-367.
International Search Report and Written Opinion, PCT/US05/17856, mailed Jul. 9, 2008.
Tenner et al., "The mTPH2 C1473G single nucleotide polymorphism is not responsible for behavioural differences between mouse strains," *Neuroscience Letters* 431:21-25 (2008).
Kulikov et al., "The C1473G polymorphism in gene tph2 is the main factor mediating the genetically defined variability of tryptophan hydroxylase-2 activity in the mouse brain," Genetika 43(12):1676-1681 (2007) (Abstract Only).
Calcagno et al., "Strain differences in basal and post-citalopram extracellular 5-HT in the mouse medial prefrontal cortex and dorsal hippocampus: relation with tryptophan hydroxylase-2 activity," *J. Neurochem.* 130:1111-1120 (2007).
Gutnecht et al., "Deficiency of brain 5-HT synthesis but serotonergic neuron formation in Tph2 knockout mice," *J. Neural Transm.* 115(8):1127-1132 (2008) (Abstract Only).

\* cited by examiner

```
hTH    445  RSYASRIQRPFSVKFDPYTLAIDVLDSPQAVRRSLEGVQDELDTLAHALSAIG  497
mTH    446  RNYASRIQRPFSVKFDPYTLAIDVLDSPHTIRRSLEGVQDELHTLTQALSAIS  498
rTH    446  RNYASRIQRPFSVKFDPYTLAIDVLDSPHTIQRSLEGVQDELHTLAHALSAIS  498 hPAH   400  RNFAATIPRPFSVRYDPYTQRIEVLDNTQQLKILADSINSEIGILCSALQKIK  452
mPAH   400  RTFAATIPRPFSVRYDPYTQRVEVLDNTQQLKNLADSINSEVGILCHALQKIKS 453
rPAH   400  RTFAATIPRPFSVRYDPYTQRVEVLDNTQQLKILADSINSEVGILCNALQKIKS 453 hTPH1  387  REFTKTIKRPFGVKYNPYTRSIQILKDTKSITSAMNELQHDLDVVSDALAKVSRKPSI  444
mTPH1  390  REFAKTVKRPFGLKYNPYTQSVQVLRDTKSITSAMNELRYDLDVISDALARVTRWPSV  447
rTPH1  387  REFAKTVKRPFGVKYNPYTQSIQVLRDSKSITSAMNELRHDLDVVNDALARVSRWPSV  444 hTPH2  433  RDFAKSITRPFESVYFNPYTQSIEILKDTRSIENVVQDLRSDLNTVCDALNKMNQYLGI  490
mTPH2  431  RDFAKSITRPFSVYFNRYTQSIEILKDTRSIENVVQDLRSDLNTVCDALNKMNQYLGI  488
rTPH2  428  RDFAKSITRPFSVYFNPYTQSIEILKDTRSIENVVQDLRSDLNTVCDALNKMNQYLGI  485
```

Fig. 2

Exon X:
CATGCTCTCTTCCGACAAGGCGTGTGTGAAATCCTTTGACCCAAAGACGACCTGCTTGCCTGCAGGAATGCC
TAATCACCACCTTTCAGGACGCTTACTTTGTTTCGGACAGTTTGAAGAAGCCAAAGAAAAGATGAG

Intron X-XI:
GTAAACCTGCTTTTCTTCCTTCTATAGAAAGTCACTTTTAAATGTCTCTCGCTGTTCCTTCTGTCTA
ACTGTTTTTTGTACCCGTGGGGTTGATTGTGTTTCCTTTTGTTTTTTTGTTATTCTACAGG
GACTT

Exon XI:
TGCAAAGTCAATTACCCGTCCCTCTCGGTATACTTCAACCSCTACACGCGAGCATTGAAATTCTG
AAAGACACCAGAGTATTGAGAATGTGGCAGGACCTGCGCAGTGATTTGAACACAGTGTGTGATG
CCTTGAATAAAATGAACCAATATCTCGGGGATTTGA

3'-UTR:
TGCCTAGAACCAGAGTTATTGTCAGCATGAGCTCTTGGGGGTGTAGCAACAATGCAGTCAATGTTA
TCCAACATCAACAACTTTCTGTGTTCATGGTTGGCTAGTAAGCATGCAATTCTGTATGTCCATACCTC
TGTGTA

Fig. 3

```
CLUSTAL W (1.8) multiple sequence alignment hPAHxx0   ------------------------MSTAVLENPGLGRKLSDFGQETSYIEDNCN
hTPH2x1   MQPAMMMESSKYWARRGFSLDSAVPEEHQLLGSSTLNKPNSG-KNDDKGNKGSSKREAAT
                                  :::.*::..* .* .*.  ::   ..

hPAHxx0   QNGAISLIFSLKEEVGALAKVLRLFEENDVNLTHIESRPSRLKKDEYEFFTHLD--KRSL
hTPH2x1   ESGKTAVVFSLKNEVGGLVKALRLFQEKRVNMVHIESRKSRRSSEVEIFVDCECGKTEF
           .*::::::*** **.*:*.:.**::*:.**:. ****:**:..: * * . *   :

hPAHxx0   PALTNIIKILR--HDIGATVHELSRDKKKDTVPWFPRTIQELDRFANQILSYGAELDADH
hTPH2x1   NELIQLLKFQTTIVTLNPPENIWTEEEELEDVPWFPRKISELDKCSHRVLMYGSELDADH
           .*::::*:   .:  ...:*.*. :..::*::* *:**: :.:.*..**** hPAHxx0   PGFKDPVYRARRKQFADIAYNYRHGQPIPRVEYMEEEKKTWGTVFKTLKSLYKTHACYEY
hTPH2x1   PGFKDNVYRQRRKYFVDVAMGYKYGQPIPRVEYTEEETKTWGVVFRELSKLYPTHACREY
          ***** *** *** *.*:*  *::*********** **:.***.**: ****  **** **

hPAHxx0   NHIFPLLEKYCGFHEDNIPQLEDVSQFLQTCTGFRLRPVAGLLSSRDFLGGLAFRVFHCT
hTPH2x1   LKNFPLLTKYCGYREDNVPQLEDVSMFLKERSGFTVRPVAGYLSPRDELAGLAYRVFHCT
           ::**** ***::**:*********:** :.*** ****** **.**:*.***.*******
```

Fig. 5 (part 1 of 2)

```
hPAHxx0    QYIRHGSKPMYTPEPDICHELLGHVPLFSDRSFAQFSQEIGLASLGAPDEYIEKLATIYW
hTPH2x1    QYIRHGSDPLYTPEPDTCHELLGHVPLLADPKFAQFSQEIGLASLGASDEDVQKLATCYF
           *****.*:.********:*********::*.**:***************.**.::.****:.

hPAHxx0    FTVEFGLCKQGDSIKAYGAGLLSSFGELQYCLSEKPKLLPLELEKTAIQNYTVTEFQPLY
hTPH2x1    FTIEFGLCKQEGQLRAYGAGLLSSIGELKHALSDKACVKAFDPKTTCLQECLITTFQEAY
           **:*******:*..:*********:***::.**:*..:*.*:**: .*.**  ** .**

hPAHxx0    YVAESFNDAKEKVRNFAATIPRPFSVRYDPYTQRIEVLDNTQQLKILADSINSEIGILCS
hTPH2x1    FVSESFEEAKEKMRDFAKSITRPFSVYFNPYTQSIEILKDTRSIENVVQDLRSDLNTVCD
           :*:***::****:*:**::*.***** :.****.**:*::*  *:   **.:*:: *..

hPAHxx0    ALQKIK------
hTPH2x1    ALNKMNQYLGI
           **:*:
```

Fig. 5 (part 2 of 2)

```
>>hPAH
MSTAVLENPGLGRKLSDFGQETSYIEDNCNQNGAISLIFSLKEEVGAL

AKVLRLFEENDVNLTHIESRPSRLKKDEYEFFTHLDKRSLPALTNIIK

ILRHDIGATVHELSRDKKKDTVPWFPRTIQELDRFANQILSYGAELDA

DHPGFKDPVYRARRKQFADIAYNYRHGQPIPRVEYMEEEKKTWGTVFK

TLKSLYKTHACYEYNHIFPLLEKYCGFHEDNIPQLEDVSQFLQTCTGF

RLRPVAGLLSSRDFLGGLAFRVFHCTQYIRHGSKPMYTPEPDICHELL

GHVPLFSDRSFAQFSQEIGLASLGAPDEYIEKLATIYWFTVEFGLCKQ

GDSIKAYGAGLLSSFGELQYCLSEKPKLLPLELEKTAIQNYTVTEFQP

LYYVAESFNDAKEKVRNFAATIPRPFSVRYDPYTQRIEVLDNTQQLKI

LADSINSEIGILCSALQKIK
```

Fig. 6

>>hTPH2
MQPAMMMFSSKYWARRGFSLDSAVPEEHQLLGSSTLNKPNSGKNDDKG

NKGSSKREAATESGKTAVVFSLKNEVGGLVKALRLFQEKRVNMVH*IE*S

RKSRRRSS*EV*EIFVDCECGKTEFNELIQLLKFQTTIVTLNPPENIWTE

EEELEDVP*WF P*RKISELDKCSHRVLMYGSELDADHPGFKDNVYRQRRK

YFVDVAMGYKYGQPIPRVEYTEEETKTWGVVFRELSKLYPTHACREYL

KNFPLLTKYC*G*YREDNVPQLEDVSMFLKERSGFTV*RP*VAGYLSP*RD*FL

AGLAYRVFHCTQYIRHGSDPL*YT*P*E*PDTCHELLGHVPLLADPKFAQFS

QEIGL*AS L*GASDEDVQKLATCYFFTIEFGLCKQEGQLRAYGAGLLSSI

GELKHALSDKACVKAFDPKTTCLQECLITTFQEAYFVSESFEEAKEKM

RDFAKSIT*R*PFSV*YF*N*PY*TQSIEILKDTRSIENVVQDLRSDLNTVCDA

LNKMNQYLGI

| hTPH2 H441/G-allele: | ATG......TCA ATT ACC CGT CCC TTC TCA......TGA |
| hTPH2 H441/A-allele: | ATG......TCA ATT ACC CAT CCC TTC TCA......TGA |

142  1463  1614

B

```
hTH    445  RSYASRIQRPFSVKFDPYTLAIDVLDSPQAVRRSLEGVQDELDTLAHALSAIG  497
mTH    446  RNYASRIQRPFSVKFDPYTLAIDVLDSPHTERRSLEGVQDELHTLTQALSAIS  498
rTH    446  RNYASRIQRPFSVKFDPYTLAIDVLDSPHTQRSLEGVQDELHTLAHALSAIS   498 hPAH   400  RNFAATIPRPFSVRYDPYTQRIEVLDNTQQLKILADSINSEIGILCSALQKIK  452
mPAH   400  RTFAATIPRPFSVRYDPYTQRVEVLDNTQQLKNLADSINSEVGILCHALQKIKS 453
rPAH   400  RTFAATIPRPFSVRYDPYTQRVEVLDNTQQLKILADSINSEVGILCNALQKIKS 453 hTPH1  387  REFTKTIKRPFGVKYNPYTRSIQILKDTKSITSAMNELQHDLDVVSDALAKVSRKPSI 444
mTPH1  390  REFAKTVKRPFGLKYNPYTQSVQVLRDTKSITSAMNELRYDLDVISDALARVTRWPSV 447
rTPH1  387  REFAKTVKRPFGVKYNPYTQSIQVIRDSKSITSAMNELRHDLDVVNDALARVSRWPSV 444 hTPH2  433  RDFAKSITRPFSVYFNPYTQSIEILKDTRSIENVVQDLRSDINTVCDALNKMNQYLGI 490
mTPH2  431  RDFAKSITRPFSVYENRYTQSIEILKDTRSIENVVQDLRSDINTVCDALNKMNQYLGI 488
rTPH2  428  RDFAKSITRPFSVYFNPYTQSIEILKDTRSIENVVQDLRSDINTVCDALNKMNQYLGI 485
```

Fig. 8a-b ion in TRYPTOPHAN
HYDROXYLASE-2 CONTROLS BRAIN
SEROTONIN SYNTHESIS

RELATED APPLICATIONS

This application claims the benefit of U.S. Provisional Patent Application Ser. No. 60/642,869 filed Jan. 11, 2005, and of U.S. Provisional Patent Application Ser. No. 60/642,800, filed Jan. 11, 2005, and of U.S. Provisional Patent Application Ser. No. 60/629,951, filed Nov. 22, 2004, and of U.S. Provisional Patent Application Ser. No. 60/606,811, filed Sep. 2, 2004, and of U.S. Provisional Patent Application Ser. No. 60/573,265, filed May 21, 2004, the disclosures of all of which are incorporated by reference herein in their entirety.

This application is related to Ranga R. Krishnan, Marc G. Caron, Xiaodong Zhang, Martin J. Beaulieu, Raul R. Gainetdinov, and Tatiana D. Sotnikova Method for Augmenting the Effects of Serotonin Reuptake Inhibitors, Ser. No. 11/133,867, filed May 20, 2005, and published as US 2006/0142375 A1 on Jun. 29, 2006, the disclosure of which is incorporated by reference herein in its entirety.

This invention was made with Government support under grant number MH60451 from the National Institutes of Health. The United States Government has certain rights to this invention.

FIELD OF THE INVENTION

The present invention concerns methods of screening for dysregulation of serotonergic neurotransmission in human or animal subjects.

BACKGROUND OF THE INVENTION

Dysregulation of serotonergic neurotransmission is an important contributing factor in many psychiatric disorders. Therefore, central serotonergic neurons are the primary targets for tricyclic antidepressants and serotonin reuptake inhibitors (SSRIs), as well as psychostimulants and hallucinogenic drugs (I. S. J. Bonasera, L. H. Tecott, *Pharmacol. Ther.* 88, 133 (2000); J. A. Gingrich, R. Hen, *Psychopharmacol.* 155, 1 (2001); D. L. Murphy et al., *Genes Brain Behav.* 2, 350 (2003)). Tryptophan hydroxylase (Tph1) has long been considered as the sole rate-limiting enzyme for the synthesis of serotonin. However, the recently cloned Tph2 is preferentially expressed in the brain, while Tph1 is mainly expressed in the periphery (D. J. Walther et al., *Science* 299, 76 (2003); M. Bader et al., PCT Application WO 2004/007704).

SUMMARY OF THE INVENTION

A first aspect of the present invention is a method of screening a subject for, detecting or diagnosing a serotonergic neurotransmission dysregulation disorder, comprising: detecting the presence or absence of an Tph2 mutation in the subject; and then determining that the subject is at increased risk of or afflicted with a serotonergic neurotransmission dysregulation disorder due to the presence or absence of the Tph2 mutation (e.g., with the presence of a mutation indicating the subject is at increased risk for or afflicted with a serotonergic neurotransmission dysregulation disorder). In some embodiments the detecting step includes a nucleic acid amplification step; in some embodiments the detecting step includes an oligonucleotide probe hybridization step.

A second aspect of the present invention is a method of treating a subject, comprising: determining the presence or absence of at least one Tph2 mutation in the subject; and then, if the subject possesses at least one Tph2 mutation, treating the subject for a serotonergic neurotransmission dysregulation disorder. In some embodiments the treating step is carried out by administering a serotonin enhancer in an amount effective to treat the disorder. In other embodiments the treating step is carried out by administering an effective drug affecting other neurotransmitter systems.

A third aspect of the present invention is a method of conducting a trial on a plurality of subjects, the method comprising: (α) determining the presence or absence of at least one Tph2 mutation in the plurality of subjects; and, before or after said determining step (a), (b) administering a test compound to the plurality of subjects; (c) detecting at least one response of the subject to the test compound; and then (d) determining the influence of the presence or absence of at least one Tph2 mutation on the response. The response may be any one, or combination of, biochemical, physiological and behavioral responses. In some embodiments the test compound is a serotonin enhancer, preferably in an amount effective to treat the disorder.

A fourth aspect of the present invention is a method for stratifying a subject in a subgroup of a clinical trial of a therapy for the treatment of a serotonergic neurotransmission dysregulation disorder, the method comprising determining the genotype of the tryptophan hydroxylase 2 gene of the subject, wherein the subject is stratified into a subgroup for the clinical trial of the therapy based upon the subject's tryptophan hydroxylase 2 genotype. In some embodiments the therapy is a serotonin enhancer therapy (i.e., administration of a serotonin enhancer in an amount effective to treat the disorder).

A fifth aspect of the present invention is an isolated nucleic acid encoding a mammalian (e.g., human) tryptophan hydroxylase 2 protein, the nucleic acid containing at least one mutation that is a risk factor for a serotonergic neurotransmission dysregulation disorder (in some embodiments an isolated mouse nucleic acid encoding an arginine at position 447 of the encoded protein as the sole mutation is excluded therefrom).

A further aspect of the present application is an isolated nucleic acid encoding a wild-type mouse tryptophan hydroxylase 2 protein (i.e., a nucleic acid encoding a proline at position 447 of the encoded protein).

A further aspect of the present invention is a recombinant nucleic acid comprising a nucleic acid as described above operatively associated with a promoter.

A further aspect of the present invention is an oligonucleotide probe (e.g., from 8 or 10 to 50 or 100 nucleotides in length) that selectively binds to a nucleic acid as described above.

A further aspect of the present invention is a host cell that contains a nucleic acid or recombinant nucleic acid as described above and expresses the encoded protein.

A further aspect of the present invention is a method of making a tryptophan hydroxylase 2 protein, comprising: culturing a cell as described above under conditions in which the encoded protein is expressed, and collecting the encoded protein from the cell.

A further aspect of the present invention is a mutant tryptophan hydroxylase 2 protein encoded by an isolated nucleic acid as described above.

A further aspect of the present invention is an antibody that selectively binds to a mutant tryptophan hydroxylase 2 protein as described herein.

A still further aspect of the present invention is the use of a means of detecting a Tph2 polymorphism or mutation in determining if a subject is afflicted with or at risk of developing dysregulation of serotonergic neurotransmission.

The foregoing and other objects and aspects of the present invention are explained in greater detail in the drawings herein and the specification set forth below.

BRIEF DESCRIPTION OF THE DRAWINGS

FIG. 2. Sequence alignment of the C-terminal regions of tyrosine hydroxylase (TH) (SEQ ID NO: 3; SEQ ID NO: 4; SEQ ID NO: 5) phenylalanine hydroxylase (PAH) (SEQ ID NO: 6; SEQ ID NO: 7; SEQ ID NO: 8), Tph1 (SEQ ID NO: 9; SEQ ID NO: 10; SEQ ID NO: 11) and Tph2 (SEQ ID NO: 12; SEQ ID NO: 13; SEQ ID NO: 14) in human (h), mouse (m) and rat (r). The highly conserved proline residues (red) and the arginine residue in mTph2 are highlighted. Numbers indicate positions of amino acid.

FIG. 3. Genotyping method for mTpb2 polymorphism of inbred mouse strains. Partial genomic DNA sequence of mTph2 is shown (SEQ ID NO: 15; SEQ ID NO: 16; SEQ ID NO: 17; SEQ ID NO: 18). Control and allele-specific primers are highlighted and indicated as arrowheads with solid and dash lines, respectively. The (C1473G) polymorphism is shown as S (S=C+G). Positions of the corresponding nucleotides (C or G) at the 3'-terminus of allele-specific primers and the deliberate mismatch at (−2) from the 3'-terminus to enhance specificity are illustrated (*).

FIG. 5 demonstrates the high sequence homology between TPH2 (SEQ ID NO: 20) and PAH (SEQ ID NO: 19), indicating functional similarity between them.

FIG. 6 shows in underlined italics lists the positions of each mutation in PAH (SEQ ID NO: 19; and FIG. 7 shows in underlined italics the corresponding positions of amino acids in TPH2 (SEQ ID NO: 20).

DETAILED DESCRIPTION OF THE PREFERRED EMBODIMENTS

Figure 1:
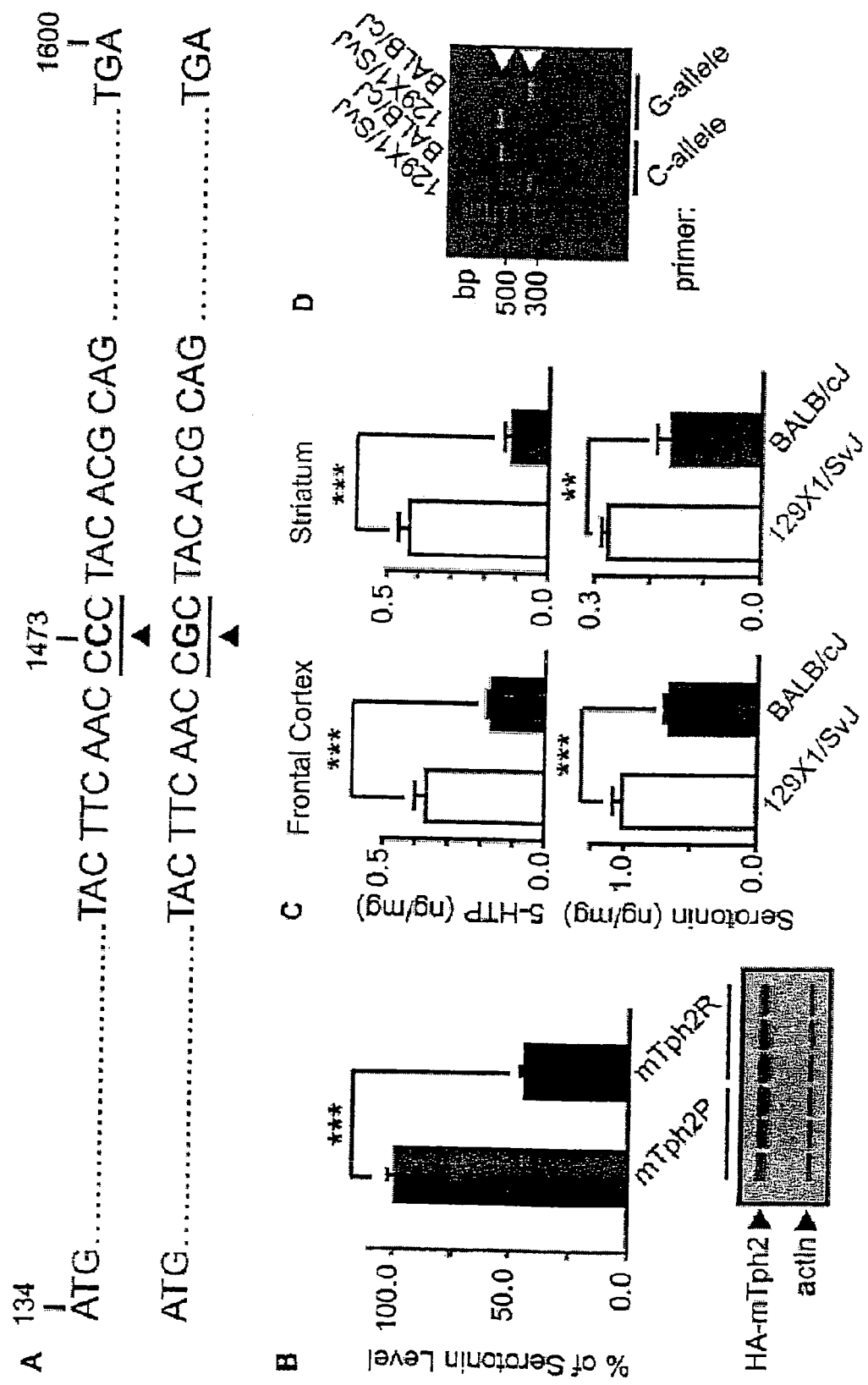
FIG. 1(A). (C1473G) polymorphism in mTph2. The C or G polymorphism are highlighted and indicated with arrowheads. Nucleotide numbers are shown for the start and stop condons of mTph2 as well as the site of polymorphism (SEQ ID NO: 1 and SEQ ID NO: 2).
FIG. 1(B). Serotonin levels in PC12 cells expressing HA-mTph2R are lower than those in PC12 cells expressing HA-mTph2P (n=6), while no differences in dopamine levels are observed. Similar levels of HA-mTph2P and HA-mTph2R are expressed in respective PC12 stable cell lines (n=3).
FIG. 1(C). BALB/cJ mice exhibit lower serotonin synthesis rates and tissue contents as compared to 129X1/SvJ mice (n=7).
FIG. 1(D). Genotyping of 129X1/SvJ and BALB/cJ mice. PCR products for positive control (523 bp) and allele-specific products (307 bp) are indicated with arrowheads. (All data are presented as means±S.E.M.s. Statistical significance of all data presented was analyzed by Student's T-test: , P<0.01; *, P<0.001.)

The present invention is explained in greater detail below. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure which do not depart from the instant invention. Hence, the following specification is intended to illustrate some particular embodiments of the invention, and not to exhaustively specify all permutations, combinations and variations thereof.

The disclosures of all United States Patent references cited herein are to be incorporated by reference herein in their entirety.

1. Definitions. "Genotyping" as used herein means determination of the type and number of alleles present in a subject, whether determined by nucleic acid sequencing, PCR or RT-PCR amplification, examination of Tph2 protein, or any other method. A specific gene can be genotyped to determine if the gene is a wild-type or variant allele. "Genotyping does not require sequencing of the entire gene but may simply involve determining the presence or absence of one or more mutations therein, as compared to the "wild type" gene.

"Serotonin enhancer" as used herein refers to any compound that increases, directly or indirectly, the availability of serotonin in the central nervous system for binding to serotonin receptors at the post-synaptic membrane, including but not limited to serotonin reuptake inhibitors, monoamine oxidase inhibitors, tricyclic antidepressants, serotonin agonists, amphetamines, serotonin precursors, serotonin prodrugs, intermediates in the biosynthesis of serotonin, co-factors and pharmaceutically acceptable salts thereof. Such compounds may be given alone or in combination with other serotonin enhancers.

"Serotonergic neurotransmission dysregulation disorder" as used herein refers to any disorder in which an increase or decrease in available serotonin contributes, at least in part, to a disease, disorder, or condition. Examples of such disorders include, but are not limited to, depressive disorder, anxiety disorder, social anxiety disorder, generalized anxiety disorder, bipolar disorder, schizophrenia, autism, epilepsy, mood disorders, alcohol or substance abuse and associated disorders, panic disorder, migraine, obesity, bulimia, anorexia, premenstrual syndrome, menopause, sleep disorders, attention-deficit/hyperactivity disorder (ADHD), Tourette syndrome, aggression, obsessive compulsive disorder, pathological gambling, novelty seeking, borderline personality disorders, antisocial personality disorder, suicidility, eating disorders, sexual dysfunction, dementia, social phobia, fibromyalgia, overactive bladder, chronic fatigue syndrome, chronic pain, sudden infant death syndrome, post-traumatic stress syndrome, and Alzheimer's disease. These terms have their usual meaning in the art (see, e.g., DSM-IV).

Subjects for screening and/or treatment with the present invention are, in general, mammalian subjects (e.g., rodent subjects such as mouse or rat, primate subjects such as human or monkey, dog, cat, rabbit, etc.), including male and female subjects. The subject may be of any race and any age, including juvenile, adolescent, and adult. It will be appreciated by those skilled in the art that, while the present methods are useful for screening subjects to provide an initial indication of the suitability of a subject for a particular treatment or study, this information may be considered by a clinician or medical practitioner in light of other factors and experience in reaching a final judgment as to the treatment which any given subject should receive.

"Treating" as used herein means the medical management of a subject, e.g., a human patient, with the intent to cure, ameliorate, stabilize, or prevent a disease, pathological condition, or disorder. This term includes active treatment, that is, treatment directed specifically toward the improvement or associated with the cure of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. "Treating" also includes symptomatic treatment, that is, treatment directed toward constitutional symptoms of the associated disease, pathological condition, or disorder. Thus "treating" includes submitting or subjecting a subject to a compound which will promote the elimination or reduction of a disease or symptoms of a disease, or which will slow the progression of said disease. For example, a subject may be treated with, synthesized organic molecules, naturally occurring organic molecules, peptides, polypeptides, nucleic acid molecules, and components thereof "Treating" also includes the act of not giving a subject a contra-indicated therapeutic.

Tryptophan hydroxylase 1 (Tph1) is known and described at GenBank accession numbers NM_004179 (human), NM_009414 (mouse); and P09810 (rat).

Tryptophan hydroxylase 2 (Tph2) is known and described at GenBank accession numbers NM_173353 (human); NM_173391 (mouse); and NM_173839 (rat). See also M. Bader and D. Walther, PCT Patent Application WO 2004/007704 (US 20060275759). These genes are referred to as the "wild type" (non-mutant) Tph2 genes herein, subject to the proviso that "wild type" when referring to mouse refers to a nucleic acid encoding a proline at position 447 of the encoded protein. Note that Walther et al. submitted the mutant (P447R) for mice at GenBank (NM_173391) and likewise in WO 2004/007704. We find and describe herein the wild type version in mice (P447) which is otherwise identical to the version previously defined in GenBank and WO 2004/007704.

Tyrosine hydroxylase (TH) is known and described at GenBank accession numbers NM_000360 (human); NM_009377 (mouse); and NM_012740 (rat).

Phenylalanine hydroxylase (Pah) is known and described at GenBank accession numbers NM_000277 (human); NM_008777 (mouse); and NM_012619 (rat).

2. Polymorphism Detection/Genotyping.

In general, the step of detecting the polymorphism of interest, or genotyping a subject, may be carried out by collecting a biological sample containing DNA from the subject, and then determining the presence or absence of DNA containing the polymorphism of interest in the biological sample. Any biological sample which contains the DNA of that subject may be employed, including tissue samples and blood samples, with blood cells being a particularly convenient source. The nucleotide sequence of the mouse and human Tph2 gene is known and suitable probes, restriction enzyme digestion techniques, or other means of detecting the polymorphism may be implemented based on this known sequence, or the variations described herein, in accordance with standard techniques. See, e.g., U.S. Pat. Nos. 6,027,896 and 5,767,248 to A. Roses et al.

In describing the mutations disclosed herein in the novel proteins described herein, and the nucleotides encoding the same, the naming method is as follows: [amino acid replaced][amino acid number in sequence of known protein][alternate amino acid]. For example, for the mouse Tph2 variant disclosed herein, proline at the 447th amino acid in the protein is replaced with arginine.

The polymorphisms described herein can be detected in accordance with known techniques based upon the known sequence information of the mouse and human Tph2 gene and the information provided herein. Novel nucleic acid sequences and proteins described herein can be isolated from human sources based upon the information provided herein or produced by other means such as site-directed mutagenesis of known or available amino acids, coupled as necessary with techniques for the production of recombinant proteins known in the art.

Determining the presence or absence of DNA containing a polymorphism or mutation of interest may be carried out with an oligonucleotide probe labeled with a suitable detectable group, or by means of an amplification reaction such as a polymerase chain reaction or ligase chain reaction (the product of which amplification reaction may then be detected with a labeled oligonucleotide probe or a number of other techniques). Further, the detecting step may include the step of detecting whether the subject is heterozygous or homozygous for the polymorphism of interest. Numerous different oligonucleotide probe assay formats are known which may be employed to carry out the present invention. See, e.g., U.S. Pat. No. 4,302,204 to Wahl et al.; U.S. Pat. No. 4,358,535 to Falkow et al.; U.S. Pat. No. 4,563,419 to Ranki et al.; and U.S. Pat. No. 4,994,373 to Stavrianopoulos et al. (applicants specifically intend that the disclosures of all U.S. Patent references cited herein be incorporated herein by reference).

Amplification of a selected, or target, nucleic acid sequence may be carried out by any suitable means. See generally D. Kwoh and T. Kwoh, Am. Biotechnol. Lab. 8, 14-25 (1990). Examples of suitable amplification techniques include, but are not limited to, polymerase chain reaction, ligase chain reaction, strand displacement amplification.(see generally G. Walker et al., Proc. Natl. Acad. Sci. USA 89, 392-396 (1992); G. Walker et al., Nucleic Acids Res. 20, 1691-1696 (1992)), transcription-based amplification (see D. Kwoh et al., Proc. Natl. Acad. Sci. USA 86, 1173-1177 (1989)), self-sustained sequence replication (or "3SR") (see J. Guatelli et al., Proc. Natl. Acad. Sci. USA 87, 1874-1878 (1990)), the Qβ replicase system (see P. Lizardi et al., BioTechnology 6, 1197-1202 (1988)), nucleic acid sequence-based amplification (or "NASBA") (see R. Lewis, Genetic Engineering News 12 (9), 1 (1992)), the repair chain reaction (or "RCR") (see R. Lewis, supra), and boomerang DNA amplification (or "BDA") (see R. Lewis, supra).

DNA amplification techniques such as the foregoing can involve the use of a probe, a pair of probes, or two pairs of probes which specifically bind to DNA containing the polymorphism of interest, but do not bind to DNA that does not contain the polymorphism of interest under the same hybridization conditions, and which serve as the primer or primers for the amplification of the DNA or a portion thereof in the amplification reaction. Such probes are sometimes referred to as amplification probes or primers herein.

In general, an oligonucleotide probe which is used to detect DNA containing a polymorphism or mutation of interest is an oligonucleotide probe which binds to DNA encoding that mutation or polymorphism, but does not bind to DNA that does not contain the mutation or polymorphism under the same hybridization conditions. The oligonucleotide probe is labeled with a suitable detectable group, such as those set forth below in connection with antibodies. Such probes are sometimes referred to as detection probes or primers herein.

Probes and primers, including those for either amplification and/or protection, are nucleotides (including naturally occurring nucleotides such as DNA and synthetic and/or modified nucleotides) are any suitable length, but are typically from 5, 6, or 8 nucleotides in length up to 40, 50 or 60 nucleotides in length, or more. Such probes and or primers may be immobilized on or coupled to a solid support such as a bead, chip, pin, or microtiter plate well in accordance with known techniques, and/or coupled to or labeled with a detectable group such as a fluorescent compound, a chemiluminescent compound, a radioactive element, or an enzyme in accordance with known techniques.

Polymerase chain reaction (PCR) may be carried out in accordance with known techniques. See, e.g., U.S. Pat. Nos. 4,683,195; 4,683,202; 4,800,159; and 4,965,188. In general, PCR involves, first, treating a nucleic acid sample (e.g., in the presence of a heat stable DNA polymerase) with one oligonucleotide primer for each strand of the specific sequence to be detected under hybridizing conditions so that an extension product of each primer is synthesized which is complementary to each nucleic acid strand, with the primers sufficiently complementary to each strand of the specific sequence to hybridize therewith so that the extension product synthesized from each primer, when it is separated from its complement, can serve as a template for synthesis of the extension product of the other primer, and then treating the sample under denaturing conditions to separate the primer extension products from their templates if the sequence or sequences to be detected are present. These steps are cyclically repeated until the desired degree of amplification is obtained. Detection of the amplified sequence may be carried out by adding to the reaction product an oligonucleotide probe capable of hybridizing to the reaction product (e.g., an oligonucleotide probe of the present invention), the probe carrying a detectable label, and then detecting the label in accordance with known techniques, or by direct visualization on a gel. When PCR conditions allow for amplification of all allelic types, the types can be distinguished by hybridization with allelic specific probe, by restriction endonuclease digestion, by electrophoresis on denaturing gradient gels, or other techniques.

Ligase chain reaction (LCR) is also carried out in accordance with known techniques. See, e.g., R. Weiss, Science 254, 1292 (1991). In general, the reaction is carried out with two pairs of oligonucleotide probes: one pair binds to one strand of the sequence to be detected; the other pair binds to the other strand of the sequence to be detected. Each pair together completely overlaps the strand to which it corresponds. The reaction is carried out by, first, denaturing (e.g., separating) the strands of the sequence to be detected, then reacting the strands with the two pairs of oligonucleotide probes in the presence of a heat stable ligase so that each pair of oligonucleotide probes is ligated together, then separating the reaction product, and then cyclically repeating the process until the sequence has been amplified to the desired degree. Detection may then be carried out in like manner as described above with respect to PCR.

It will be readily appreciated that the detecting steps described herein may be carried out directly or indirectly. For example, a polymorphism or mutation could be detected by measuring by digestion with restriction enzymes, detection of markers that are linked to the mutation or polymorphism, etc.

Genotype determinations can be compiled to predict either prognosis, drug efficacy, or suitability of a patient for participating in clinical trials of a neurological disease therapeutic. For example, the genotype may be compiled with other patient parameters such as age, sex, disease diagnosis, and known allelic frequency of a representative control population. A determination of the statistical probability of the patient having a particular disease risk, drug response, or patient outcome may be assessed from such genotype determinations. Patient outcome, i.e. a prediction of a patient's likely health status, may include a prediction of the patient's response to therapy, rehabilitation time, recovery time, cure rate, rate of disease progression, predisposition for future disease, or risk of having relapse.

Kits useful for carrying out the methods of the present invention will, in general, comprise one or more oligonucleotide probes and other reagents for carrying out the methods as described above, such as restriction enzymes, optionally packaged with suitable instructions for carrying out the methods.

The new polymorphisms described herein provide novel nucleic acids encoding the mammalian (e.g., mouse or human) Tph2, along with probes such as described above that bind selectively thereto. Such nucleic acids can be inserted into vectors such as plasmids, optionally associated with or placed under the control of a promoter, and the nucleic acids may be inserted into host cells and optionally expressed therein (when the promoter is operative in the host cell) to produce Tph2.

Particular examples of mutations of interest useful for carrying out the present invention, are those where the Tph2 is human Tph2 and the mutation encodes a change in an amino acid of the encoded protein, said amino acid selected from the group consisting of A65, V66, F68, L77, F84, I94, R97, E105, P152, W153, P155, D162, L175, R191, E211, V223, P244, G251, R276, P277, V278, R285, R294, P308, Y310, E313, A333, I339, A342, S343 ,L344, A346, K353, V421, E423, A428, A436, R441, Y446, P449, Y450, and Q468. Corresponding mutations in the corresponding locations of other species based upon alignment of the sequences are also useful in carrying out the present invention, even though the aligned position of the specific amino acid may differ. A mutation inducing any change in the normal sequence (the amino acid to the left of the number identifying the amino acid location) is within the scope of the present invention (for example, a change of: I to T; E to G; P to Q; R to Q; G to V; P to L; R to W; Y to D; E to K; L to P; R to Q; Y to C; R to H; P to R; A to V; V to I; L to V; Q to X (where X is a stop codon) etc.).

Specific examples of mutations useful for carrying out the present invention are the human P449R mutation, the human R441H mutation, the human W153R mutation, the human A65V mutation, the human V66I mutation, the human L175V mutation, and the human Q468X (where X is a stop codon) mutation. Subjects may be determined to be heterozygous or homozygous for the indicated mutation, or may be determined to carry diferent mutations on the same, or different, alleles.

Note that 43 mutations are identified herein, some identified by sequence analysis and some by sequence identity compared to PAH. Table 1 below lists corresponding mutations in Tph2 in six different species, which corresponding mutations are also useful for carrying out the present invention. It is striking that all 43 amino acids for these mutations are virtually identical in Tph2 in six different species (except in two positions). This strongly indicates that mutations in similar position in Tph2 have a like functional impact on serotonin production in other species.

In addition to the foregoing, intronic mutations are useful for carrying out the present invention. For example, a G→A mutation at position 144 in Intron 6 of human TPH2 is useful for carrying out the present invention. This is a non-coding mutation in the Intron 6 and is predicted to cause an alternative splicing variant/mutation of human TPH2. The entire intron 6 in human TPH2 is 6236 base pairs in length; the pertinent portion of exon 6 is shown in panel a of Table 2 below, and the pertinint portion of the mutant intron 6 is shown in panel B of Table 2 below.

TABLE 1

Corresponding mutations in additional species.

| human | mouse | rat | chicken | zebrafish | pufferfish |
|---|---|---|---|---|---|
| A65 | A63 | A60 | A64 | A35 | A61 |
| V66 | V64 | V61 | V65 | V36 | V62 |
| F68 | F66 | F63 | F67 | F38 | F64 |
| L77 | L75 | L72 | L76 | L47 | L73 |
| F84 | F82 | F79 | F83 | F54 | F80 |
| I94 | I92 | I89 | I93 | I64 | I90 |
| R97 | R95 | R92 | R96 | R67 | R93 |
| E105 | E103 | E100 | E104 | E75 | E101 |
| P152 | P150 | P147 | P151 | P135 | P148 |
| W153 | W151 | W148 | W152 | W136 | W149 |
| P155 | P153 | P150 | P154 | P138 | P151 |
| D162 | D160 | D157 | D161 | D145 | D158 |
| L175 | L173 | L170 | L174 | L158 | L171 |
| R191 | R189 | R186 | R190 | R174 | R187 |
| E211 | E209 | E206 | E210 | E194 | E207 |
| V223 | V221 | V218 | V222 | V206 | V219 |
| P244 | P242 | P239 | P243 | P227 | P240 |
| G251 | G249 | G246 | G250 | G234 | G247 |
| R276 | R274 | R271 | R275 | R259 | R272 |
| P277 | P275 | P272 | P276 | P260 | P273 |
| V278 | V276 | V273 | V277 | V261 | V274 |
| R285 | R283 | R280 | R284 | R268 | R281 |
| R294 | R292 | R289 | R293 | R277 | R290 |
| P308 | P306 | P303 | P307 | P291 | P304 |
| Y310 | Y308 | Y305 | Y309 | Y293 | Y306 |

TABLE 1-continued

Corresponding mutations in additional species.

| human | mouse | rat | chicken | zebrafish | pufferfish |
|---|---|---|---|---|---|
| E313 | E311 | E308 | E312 | Y296 | E309 |
| A333 | A331 | A328 | A332 | A316 | A329 |
| I339 | I337 | I334 | I338 | I322 | I335 |
| A342 | A340 | A337 | A341 | A325 | A338 |
| S343 | S341 | S338 | S342 | S326 | S339 |
| L344 | L342 | L339 | L343 | L327 | L340 |
| A346 | A344 | A341 | A345 | A329 | A342 |
| K353 | K351 | K348 | K352 | K336 | K349 |
| V421 | V419 | V416 | V420 | V404 | V417 |
| E423 |  | E418 | E422 | E406 | E419 |
| A428 | A426 | A423 | A427 | A411 | A424 |
| A436 | A434 | A431 | A435 | A419 | A432 |
| R441 | R439 | R436 | R440 | R424 | R437 |
| Y446 | Y444 | Y441 | Y445 | Y429 | Y442 |
| P449 | P447 | P444 | P448 | P432 | P445 |
| Y450 | Y448 | Y445 | Y449 | Y433 | Y446 |
| Q468 | Q466 | Q463 | Q467 |  | Q464 |

TABLE 2

Intron 6 non-coding mutation.

| | | |
|---|---|---|
| A | GGTCAGCCCATTCCCAGGGTGGAGTATACTGAAGAAGAAACTAAAACT<br>TGGGGTGTTGTATTCCGGGAGCTCTCCAAACTCTATCCCACTCATGCT<br>TGCCGAGAGTATTTGAAAAACTTCCCTCTGCTGACTAAATACTGTGGC<br>TACAGAGAGGACAATGTGCCTCAACTCGAAGATGTCTCCATGTTTCTG<br>AAAG | (SEQ ID NO: 23) |
| B | gtaagatttcacacaggctgtctcttattagtcaatatcctcaattgc<br>cttccaaggacacaggttgcagcaatggctcttttccaaaaaaggaa<br>aaacagtgatttaaaaaattgttggctttgagccaacaattacctgcg<br>gccacctgtgggaagcagagcaagggactcagctgcttttgcagctca<br>ggagcttgctgaggcctctttgtggctggttgttgtaaatggtaaggc<br>ccaaaggatatttgcaagttcagctctgagcttttctgatccaggag<br>ctgctgtgctgggctacatgagtatgaaatgacctccaaaagtgcctt<br>tttatttgctttgttaaaaagtat | (SEQ ID NO: 24) |

The g/a polymorphism is shown in bold underlined font in panel b.

The g/a polymorphism is shown in bold underlined font in panel b.

3. Recombinant Nucleic Acids and Protein Production.

The production of cloned genes, recombinant DNA, vectors, transformed host cells, proteins and protein fragments by genetic engineering is well known. See. e.g., U.S. Pat. No. 4,761,371 to Bell et al. at Col. 6 line 3 to Col. 9 line 65; U.S. Pat. No. 4,877,729 to Clark et al. at Col. 4 line 38 to Col. 7 line 6; U.S. Pat. No. 4,912,038 to Schilling at Col. 3 line 26 to Col. 14 line 12; and U.S. Pat. No. 4,879,224 to Wallner at Col. 6 line 8 to Col. 8 line 59. (Applicant specifically intends that the disclosure of all patent references cited herein be incorporated herein in their entirety by reference).

Methods for DNA sequencing which are well known and generally available in the art may be used to practice any of the embodiments of the invention. The methods may employ such enzymes as the Klenow fragment of DNA polymerase I, SEQUENASE® (US Biochemical Corp, Cleveland, Ohio), Taq polymerase (Perkin Elmer), thermostable T7 polymerase (Amersham, Chicago, Ill.), or combinations of polymerases and proofreading exonucleases such as those found in the ELONGASE Amplification System marketed by Gibco/BRL (Gaithersburg, Md.). Preferably, the process is automated with machines such as the Hamilton Micro Lab 2200 (Hamilton, Reno, Nev.), Peltier Thermal Cycler (PTC200; MJ Research, Watertown, Mass.) and the ABI Catalyst and 373 and 377 DNA Sequencers (Perkin Elmer).

The nucleic acid sequences encoding the protein or peptide of the invention may be extended utilizing a partial nucleotide sequence and employing various methods known in the art to detect upstream sequences such as promoters and regulatory elements. For example, one method which may be employed, "restriction-site" PCR, uses universal primers to retrieve unknown sequence adjacent to a known locus (Sarkar, G. (1993) PCR Methods Applic. 2, 318-322). In particular, genomic DNA is first amplified in the presence of primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

A vector is a replicable DNA construct. Vectors are used herein either to amplify DNA encoding the proteins of the present invention or to express the proteins of the present invention. An expression vector is a replicable DNA construct in which a DNA sequence encoding the proteins of the present invention is operably linked to suitable control sequences capable of effecting the expression of proteins of the present invention in a suitable host. The need for such control sequences will vary depending upon the host selected and the transformation method chosen. Generally, control sequences include a transcriptional promoter, an optional operator sequence to control transcription, a sequence encoding suitable mRNA ribosomal binding sites, and sequences which control the termination of transcription and translation. Amplification vectors do not require expression control domains. All that is needed is the ability to replicate in a host, usually conferred by an origin of replication, and a selection gene to facilitate recognition of transformants.

Vectors comprise plasmids, viruses (e.g., adenovirus, cytomegalovirus), phage, retroviruses and integratable DNA fragments (i.e., fragments integratable into the host genome by recombination). The vector replicates and functions independently of the host genome, or may, in some instances, integrate into the genome itself. Expression vectors should contain a promoter and RNA binding sites which are operably linked to the gene to be expressed and are operable in the host organism. DNA regions are operably linked or operably associated when they are functionally related to each other. For example, a promoter is operably linked to a coding sequence if it controls the transcription of the sequence; a ribosome binding site is operably linked to a coding sequence if it is positioned so as to permit translation. Generally, operably linked means contiguous and, in the case of leader sequences, contiguous and in reading phase.

Transformed host cells are cells which have been transformed or transfected with vectors containing DNA coding for proteins of the present invention need not express protein.

Suitable host cells include prokaryotes, yeast cells, or higher eukaryotic organism cells. Prokaryote host cells include gram negative or gram positive organisms, for example Escherichia coli (E.coli) or Bacilli. Higher eukaryotic cells include established cell lines of mammalian origin as described below. Exemplary host cells are E.coli W3110 (ATCC 27,325), E.coli B, E.coli X1776 (ATCC 31,537), E.coli 294 (ATCC 31,446).

Expression vectors should contain a promoter which is recognized by the host organism. This generally means a promoter obtained from the intended host. Promoters most commonly used in recombinant microbial expression vectors include the beta-lactamase (penicillinase) and lactose promoter systems (Chang et al., Nature 275, 615 (1978); and Goeddel et al., Nature 281, 544 (1979), a tryptophan (trp) promoter system (Goeddel et al., Nucleic Acids Res. 8, 4057 (1980) and EPO App. Publ. No. 36,776) and the tac promoter (H. De Boer et al., Proc. Natl. Acad. Sci. USA 80, 21 (1983). While these are commonly used, other microbial promoters are suitable. Details concerning nucleotide sequences of many have been published, enabling a skilled worker to operably ligate them to DNA encoding the protein in plasmid or viral vectors (Siebenlist et al., Cell 20, 269 (1980). The promoter and Shine-Dalgarno sequence (for prokaryotic host expression) are operably linked to the DNA encoding the desired protein, i.e., they are positioned so as to promote transcription of the protein messenger RNA from the DNA.

Cultures of cells derived from multicellular organisms are a desirable host for recombinant protein synthesis. In principal, any higher eukaryotic cell culture is workable, whether from vertebrate or invertebrate culture, including insect cells. Propagation of such cells in cell culture has become a routine procedure. See Tissue Culture, Academic Press, Kruse and Patterson, editors (1973). Examples of useful host cell lines are VERO and HeLa cells, Chinese hamster ovary (CHO) cell lines, and WI138, BHK, COS-7, CV, and MDCK cell lines. Expression vectors for such tells ordinarily include (if necessary) an origin of replication, a promoter located upstream from the gene to be expressed, along with a ribosome binding site, RNA splice site (if intron-containing genomic DNA is used), a polyadenylation site, and a transcriptional termination sequence.

The transcriptional and translational control sequences in expression vectors to be used in transforming vertebrate cells are often provided by viral sources. For example, commonly used promoters are derived from polyoma, Adenovirus 2, and Simian Virus 40 (SV40). See, e.g., U.S. Pat. No. 4,599,308. The early and late promoters are useful because both are obtained easily from the virus as a fragment which also contains the SV40 viral origin of replication. See Fiers et al., Nature 273, 113 (1978). Further, the protein promoter, control and/or signal sequences, may also be used, provided such control sequences are compatible with the host cell chosen.

An origin of replication may be provided either by construction of the vector to include an exogenous origin, such as may be derived from SV40 or other viral source (e.g. Polyoma, Adenovirus, VSV, or BPV), or may be provided by the host cell chromosomal replication mechanism. If the vector is integrated into the host cell chromosome, the latter may be sufficient.

Host cells such as insect cells (e.g., cultured Spodoptera frugiperda cells) and expression vectors such as the baculorivus expression vector (e.g., vectors derived from Autographa californica MNPV, Trichoplusia ni MNPV, Rachiplusia ou MNPV, or Galleria ou MNPV) may be employed to make proteins useful in carrying out the present invention, as described in U.S. Pat. Nos. 4,745,051 and 4,879,236 to Smith et al. In general, a baculovirus expression vector comprises a baculovirus genome containing the gene to be expressed inserted into the polyhedrin gene at a position ranging from the polyhedrin transcriptional start signal to the ATG start site and under the transcriptional control of a baculovirus polyhedrin promoter.

In mammalian host cells, a number of viral-based expression systems may be utilized. In cases where an adenovirus is used as an expression vector, sequences of the invention may be ligated into an adenovirus transcription/translation complex consisting of the late promoter and tripartite leader sequence. Insertion in a non-essential E1 or E3 region of the viral genome may be used to obtain a viable virus which is capable of expressing the protein or peptide of the invention in infected host cells (Logan, J. and Shenk, T. (1984) Proc.

*Natl. Acad Sci.* 81:3655-3659). In addition, transcription enhancers, such as the Rous sarcoma virus (RSV) enhancer, may be used to increase expression in mammalian host cells.

Rather than using vectors which contain viral origins of replication, one can transform mammalian cells by the method of cotransformation with a selectable marker and the chimeric protein DNA. An example of a suitable selectable marker is dihydrofolate reductase (DHFR) or thymidine kinase. See U.S. Pat. No. 4,399,216. Such markers are proteins, generally enzymes, that enable the identification of transform ant cells, i.e., cells which are competent to take up exogenous DNA. Generally, identification is by survival or transformants in culture medium that is toxic, or from which the cells cannot obtain critical nutrition without having taken up the marker protein.

As noted above, the present invention provides isolated and purified proteins and peptides, such as mammalian (dog, cat, goat, horse, sheep, rabbit, human, mouse and rat) proteins or peptides. Such proteins or peptides can be purified from host cells which express the same, in accordance with known techniques, or even manufactured synthetically.

Nucleic acids of the present invention, constructs containing the same and host cells that express the encoded proteins are useful for making proteins of the present invention.

Proteins of the present invention are useful as immunogens for making antibodies as described herein, and these antibodies and proteins provide a "specific binding pair." Such specific binding pairs are useful as components of a variety of immunoassays and purification techniques, as is known in the art, and are useful in immunoassays for carrying out the subject screening procedures described herein. In addition the proteins of the invention may be used in vitro for drug development and drug screening purposes.

Host cells transformed with nucleotide sequences encoding a protein or peptide of the invention may be cultured under conditions suitable for the expression and recovery of the protein from cell culture. The protein produced by a transformed cell may be secreted or contained intracellularly depending on the sequence and/or the vector used. As will be understood by those of skill in the art, expression vectors containing polynucleotides which encode a protein or peptide of the invention may be designed to contain signal sequences which direct secretion of the protein or peptide through a prokaryotic or eukaryotic cell membrane. Other constructions may be used to join sequences encoding the protein or peptide to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.).

Antibodies that specifically bind to the proteins of the present invention (i.e., antibodies which bind to a single antigenic site or epitope on the proteins) are useful for a variety of diagnostic purposes.

Antibodies to the protein or peptide of the invention may be generated using methods that are well known in the art. Such antibodies may include, but are not limited to, polyclonal, monoclonal, chimeric, single chain, Fab fragments, and fragments produced by a Fab expression library. Neutralizing antibodies, (i.e., those which inhibit dimer formation) are especially preferred for therapeutic use.

For the production of antibodies, various hosts including goats, rabbits, rats, mice, humans, and others, may be immunized by injection with the protein or peptide of the invention or any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and Corynebacterium parvum are especially preferable.

Monoclonal antibodies to the protein or peptide of the invention may be prepared using any technique which provides for the production of antibody molecules by continuous cell lines in culture. These include, but are not limited to, the hybridoma technique, the human B-cell hybridoma technique, and the EBV-hybridoma technique. See, e.g., Kohler, G. et al. (1975) *Nature,* 256, 495-497; Kozbor, D. et al. (1985) *J. Immunol. Methods* 81, 31-42; Cote, R. J. et al. (1983) *Proc. Natl. Acad. Sci. USA* 80, 2026-2030; Cole, S. P. et al. (1984) *Mol. Cell Biol.* 62,109-120.

4. Therapeutic Treatments.

In addition to their use in determining if a subject is at risk of a particular disorder or confirming a diagnosis of a particular disorder, the polymorphism detection or genotyping techniques described herein can be used to determine the potential benefit of treating a subject with a serotonin enhancer or alternative therapy, with subjects found to have a mutation as described herein being indicated to receive greater or less clinical benefit from a serotonin enhancer therapy than those who do not. If not receiving a serotonin enhance therapy, a subject screened or genotyped according to the present invention and found to contain a Tph2 mutation may be administered a serotonin enhancer or other appropriate treatment as a therapy for a serotonin neurotransmission dysregulation disorder; if receiving a serotonin enhancer therapy, a subject screened or genotyped according to the present invention and not found to contain a Tph2 mutation may have a previously prescribed serotonin enhancer therapy discontinued in favor of an alternate treatment, or adjusted to include other suitable treatments in addition to the serotonin enhancer therapy. Depending upon the subject's genotype and the presence or absence of Tph2 mutations, a serotonin enhance therapy of greater selectivity (e.g., in some embodiments where mutations are present; in other embodiments where mutations are absent) or lesser selectivity (e.g., in some embodiments where mutations are absent; in other embodiments where mutations are present) for serotonin neurotransmission can be administered to the subject.

Serotonin enhancers. Numerous serotonin enhancers and serotonin enhancer therapies are known. See, e.g, U.S. Pat. No. 6,218,395. The serotonin enhancer can be a serotonin reuptake inhibitor or selective serotonin reuptake inhibitor, such as described in U.S. Pat. Nos. 6,552,014; 6,492,366; 6,387,956; 6,369,051; or 5,958,429. Examples of selective serotonin reuptake inhibitors include, but are not limited to, Citalopram, fluvoxamine, floxetine, sertraline, paroxetine, etc. The serotonin enhancer can be a monoamine oxidase inhibitor such as described in U.S. Pat. Nos. 6,472,423 and 6,011,054. Examples of monoamine oxidase inhibitors include but are not limited to Isocarboxazid, phenelzine, and tranylcypromine. The serotonin enhancer can be a serotonin agonist such as described in U.S. Pat. Nos. 6,656,172;-6,579, 899 and 6,387,907. The serotonin enhancer can be an amphetamine (including derivatives thereof such as phentermine, fenfluramine, and (+)-3,4-methylenedioxyamphetamine. The serotonin enhancer can be a tricyclic antidepressant such as described in U.S. Pat. Nos. 6,368,814; 6,358,944; 6,239,162; and 6,211,171. Examples of tricyclic antidepressants include but are not limited to imipramine, amitriptyline and clomipramine. The serotonin enhancer can be an anxiolytic such as buspirone or ipsapirone. The serotonin enhancer can be a precursor or prodrug of serotonin, or an intermediate in serotonin biosynthesis, such as described in U.S. Pat. Nos. 6,579,899; 6,013,622; and 5,595,772. An example includes tryptophan, 5-hydroxytryptophan, TPH2 co-factor tetrahydrobiopterin and its precursors, a tryptophan-rich diet or dietary supplements of tryptophan.

5. Clinical Trials.

In addition to their use in the diagnosis, prognosis, or screening for disorders, detection of mutations in Tph2 can be used in conducting a clinical trial in like manner as other genotype information is used to conduct a clinical trial such as described in (for example) U.S. Pat. Nos. 6,573,049; 6,368, 797; and 6,291,175. In some embodiments such methods advantageously permit the refinement of the patient population so that advantages of particular treatment regimens (typically administration of pharmaceutically active organic compound active agents) can be more accurately detected, particularly with respect to particular sub-populations of patients. In some embodiments, such methods comprise administering a test active agent or therapy to a plurality of subjects (a control or placebo therapy typically being administered to a separate but similarly characterized plurality of subjects) and detecting the presence or absence of at least one mutation or polymorphism as described above in the plurality of subjects. The polymorphisms may be detected before, after, or concurrently with the step of administering the test therapy. The influence of one or more detected polymorphisms or absent polymorphisms on the test therapy can then be determined on any suitable parameter or potential treatment outcome or consequence, including but not limited to: the efficacy of said therapy, lack of side effects of the therapy, etc.

For example, a clinical trial can be set up to test the efficacy of test compounds to treat any number of diseases for which a Tph2 mutation has been determined to be associated with a subject diagnosed with a disease or at risk for developing the disease. If subjects are genotyped after the completion of a clinical trial, the analyses may still be aimed a determining a relationship between a treatment for a disease and the allele to be assessed for efficacy. Alternatively, if a symptomatic subject has not yet been diagnosed with the disease but has been determined to be at risk, a similar clinical trial to the clinical trial described above may be carried out. Assessment of the efficacy of a drug chosen for the trial may include monitoring the subject over a period of time, and analyzing the delay of onset of the disease and the intensity of the disease at the time of onset, as well as measuring the onset of symptoms which are associated with the disease. A drug, that in a clinical trial eliminates or delays the onset of the disease, or reduces the symptoms of the disease may be a beneficial drug to use in patients that are determined to be at risk for developing a disease. Test compounds which may be used in such trials include serotonin enhancers as described above, including those previously approved for clinical use and new compounds not yet approved for use, or approved for treating a particular disease. Thus part of the clinical trial may include the optimization of drug administration, including dosage, timing of administration, toxicities or side effects, route of administration, and efficacy of the treatment.

The present invention is explained in greater detail in the following non-limiting Examples.

EXAMPLE 1

The Pro447Arg (C1473G) Mutation

To study the biological function of Tph2, we performed RT-PCR to obtain cDNA of Tph2 from brainstem tissue combined from mice of different genotypes (see materials and methods below). We obtained two different clones of mTph2 encoding either Arg447 (CGC, mTph2R) or Pro447 (CCC, mTph2P) (FIG. 1A). Comparison with other members of this family of enzymes, tyrosine hydroxylase, phenylalanine hydroxylase and Tph1 in human, mouse and rat, as well as with mouse genome sequence, revealed that Pro447 was highly conserved (FIG. 2). Therefore, we decided to explore the possible consequences of this (C1473G) polymorphism. We used PC12 cells that endogenously synthesize dopamine and norepinephrine (L. A. Greene, A. S. Tischler, *Proc. Natl. Acad. Sci. U.S.A.* 73, 2424 (1976)) and generated stable cell lines that express similar levels of hemagglutinin (HA)-tagged mTph2P and mTph2R, respectively (FIG. 1B). Serotonin levels in PC12 cells expressing HA-mTph2R were reduced by ~55% as compared to those-in PC12 cells expressing HA-mTph2P (FIG. 1B), whereas no serotonin was detected in mock-transfected PC12 cells.

We then applied a modified tetra-primer amplification refractory mutation system (ARMS)-PCR (S. Ye, S. Dhillon, X. Ke, A. R. Collins, I. N. Day, *Nucleic Acids Res.* 29, E88 (2001)) with C- or G-allele specific primers to identify the mouse strain(s) that harbored the (C1473G) polymorphism (FIG. 3). We first tested 129X1/SvJ and BALB/cJ mice that display significant serotonin-related behavioral differences (I. Lucki, A. Dalvi, A. J. Mayorga, *Psychopharmacol.* 155, 315 (2001)) and identified that 129X1/SvJ mice were homozygous for the 1473C allele, whereas BALB/cJ mice were homozygous for the 1473G allele (FIG. 1D, Table 3).

TABLE 3

List of inbred mouse strains that have been genotyped for mTph2 (C1473G) polymorphism.

| Source | Strain | n | Allele C/C | C/G | G/G |
|---|---|---|---|---|---|
| Jackson Laboratory | C57Bl/6J | 116 | + | | |
| | 129X1/SvJ | 31 | + | | |
| | BALB/cJ | 27 | | | + |
| | DBA/2J | 9 | | | + |
| Charles River | C57Bl/6NCrlBR | 25 | + | | |
| | BALB/cAnNCrlBR | 5 | | | + |
| | DBA/2NCrlBR | 5 | | | + |
| Harlan | C57Bl/6NHsd | 5 | + | | |
| Hilltop | C57Bl/6NHlaCVF | 5 | + | | |
| | BALB/cHlaCVF | 5 | | | + |

Figure 4:
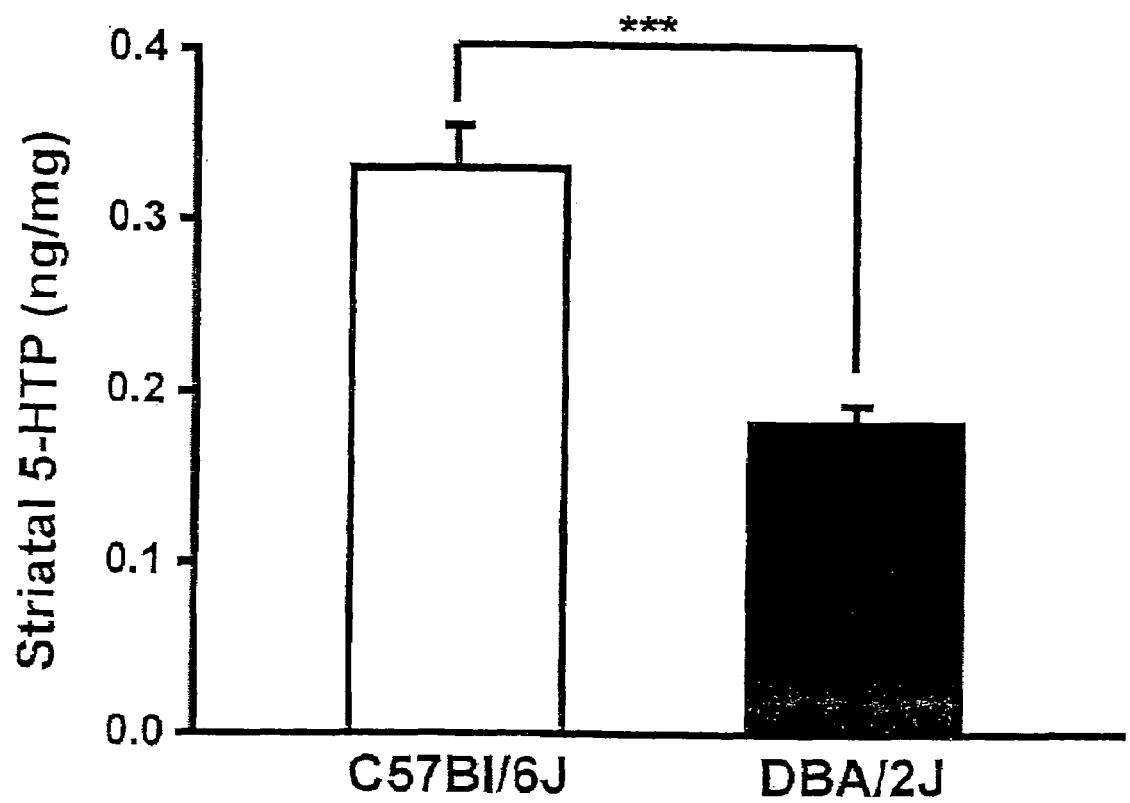
FIG. 4. DBA/2J mice exhibit lower striatal 5-HTP synthesis as compared to C57B1/6J mice (n=8). (All data are presented as means±S.E.M.s. Statistical significance of all data presented was analyzed by Student's T-test: ***, P<0.001).

Next, we carried out experiments to determine in vivo serotonin synthesis in 129X1/SvJ and BALB/cJ mice (see materials and methods below). We treated mice with m-hydroxybenzylhydrazine to determine the accumulation of the serotonin precursor, 5-hydroxytryptophan (5-HTP) and found BALB/cJ mice showed ~50% and ~70% reduction in 5-HTP synthesis in frontal cortex and striatum, respectively, as compared to 129X1/SvJ mice (FIG. 1C, Upper panel). Similarly, tissue contents of serotonin in untreated mice were measured and revealed a substantial ~40% decrease in frontal cortex and striatum of BALB/cJ mice as compared to those in 129X1/SvJ mice (FIG. 1C, Lower panel). Importantly, no significant differences of mTph2 mRNA levels in brainstem tissue between 129X1/SvJ and BALB/cJ strains were detected (data not shown). Further genotyping revealed the existence of homozygous 1473C allele in C57B1/6 mice and homozygous 1473G allele in DBA/2 mice (Table 3) that also showed ~45% difference in striatal 5-HTP synthesis (FIG. 4).

Because mice of these strains are widely used in biomedical research, identification of this functional polymorphism has immediate practical impact.

The same polymorphism, human P449R, has been also identified in human TPH2.

Variations in brain serotonin levels can contribute to behavioral differences in mice (I. Lucki, A. Dalvi, A. J. Mayorga, *Psychopharmacol.* 155, 315 (2001); R. R. Gainetdinov et al., *Science* 283, 397 (1999)) and psychiatric disorders in human (S. J. Bonasera, L. H. Tecott, *Pharmacol. Ther.* 88, 133 (2000); 2. J. A. Gingrich, R. Hen, *Psychopharmacol.* 155, 1 (2001); D. L. Murphy et al., *Genes Brain Behav.* 2, 350 (2003)). However, the underlying mechanism(s) for these differences has yet to be elucidated. Our data provide direct evidence for the fundamental role of Tph2 in serotonin synthesis in the central nervous system and set the stage for a better understanding of serotonin-related behaviors in mice and psychiatric disorders in human.

Materials and Methods

Mice. All experiments were conducted in accordance with NIH guidelines for the care and use of animals and with an approved animal protocol from the Duke University Animal Care and Use Committee. Mice from different sources (Table 1) were housed four or five to a cage, maintained under standard lab conditions (12-hour light/dark cycle) with food and water provided ad libitum, and tested at 8-week of age.

RT-PCR and mammalian expression constructs for mTph2. Total RNA from mouse brainstem tissue was extracted using TRI reagent and RT-PCR kit was used to obtain first-strand cDNA. Mouse Tph2 was then amplified with pfu DNA polymerase using specific primers. The PCR product was digested with EcoR V (GATATC) and Xba I (TCTAGA), and ligated into a pcDNA3 vector containing N-terminal triple-HA tag.

Genotyping and PCR conditions. ARMS-PCR (FIG. 3) genotyping was performed on mice genomic DNA and PCR conditions were as follow: 1 cycle (5 min at 94° C.) and 40 cycles (30 s at 94° C., 30 s at 60° C., 30 s at 72° C.) using Taq DNA polymerase (S. Ye, S. Dhillon, X. Ke, A. R. Collins, I. N. Day, *Nucleic Acids Res.* 29, E88 (2001)). The PCR reactions were carried out with primers for positive control (mOuter/Forward and mOuter/Reverse) plus either C-allele or G-allele specific primer.

Neurochemical Assessments. For monoamine analysis, mouse brain regions were dissected and monoamines were extracted and analyzed for levels of serotonin and 5-HTP using HPLC by electrochemical detection. To assess serotonin synthesis rate in vivo, mice were treated with 100 mg/kg (i.p.) of m-hydroxybenzylhydrazine for 1 hr and brain regions were dissected for analysis of 5-HTP. To determine dopamine and serotonin levels in PC12 cells, five million cells were homogenized in 200 μl 0.1 M $HClO_4$, centrifuged and filtered. Supernatants were then analyzed by HPLC (F. Xu et al., *Nat. Neurosci.* 3, 465 (2000)). Serotonin levels in PC12 cells were normalized to dopamine levels measured in the same sample.

GenBank accession number. Tph1 (human, NM_004179; mouse, NM_009414; rat, P09810), Tph2 (human, NM_173353; mouse, NM_173391; rat, NM_173839), TH (human, NM_000360; mouse, NM_009377; rat, NM_012740), Pah (human, NM_000277; mouse, NM_008777; rat, NM_012619).

EXAMPLE 2

Additional Mutations Based Upon

Phenylalanine Hydroxylase (PAH) Homology

FIG. 5 demonstrates the high sequence homology between TPH2 and PAH, indicating functional similarity between them. The amino acids shown in underlined italics red are those whose mutations have been identified and characterized in PAH. These mutations consist of about 45% of total population of phenylketonuria (PKU) and patients have symptoms varying from mild to severe PKU. In addition, these amino Primer information.

mTph2 cloning primers:

| | |
|---|---|
| forward primer, | (5'-ACCGATATCATGCAGCCCGCAATGATGA) (SEQ ID NO: 25); |
| reverse primer, | (5'-AAATCTAGATTGCTACACCCCCAAGAGCT) (SEQ ID NO: 26). |

Genotyping primers:

| | |
|---|---|
| mOuter/Forward primer, | (5'-TTTGACCCAAAGACGACCTGCTTGCA) (SEQ ID NO: 27); |
| mOuter/Reverse primer, | (5'-TGCATGCTTACTAGCCAACCATGACACA) (SEQ ID NO: 28); |
| C-allele specific primer, | (5'-CAGAATTTCAATGCTCTGCGTGTGGG) (SEQ ID NO: 29); |
| G-allele specific primer, | (5'-CAGAATTTCAATGCTCTGCGTGTGGC) (SEQ ID NO: 30). |

Generation of PC12 cell lines stably expressing HA-mTph2P and HA-mTph2R. PC12 cells were transfected by electroporation with HA-mTph2P or HA-mTph2R along with pEF6 His A vector which contains a Blasticidin-resistance gene. Stable PC12 cell lines expressing HA-mTph2P and HA-mTph2R were selected in the presence of 5 μg/ml of Blasticidin in DMEM medium supplemented with 5% bovine calf serum and 5% equine serum in 10% $CO_2$ incubator. Expression of mTph2 was confirmed by Western blotting using HA monoclonal antibody.

acids are highly conserved between TPH2 and PAH, except one shown in green. The amino acid highlighted in blue is the one we found in mice, but there is no report of this mutation in PAH yet.

FIG. 6 shows in underlined italics lists the positions of each mutation in PAH and FIG. 7 shows in underlined italics the corresponding positions of amino acids in TPH2. Due to the high sequence homology between PAH and TPH2, the consequences of having similar mutations in TPH2 can be predicted, and a serotonergic neurotransmission dysregulation disorder is indicated if any of the amino acids shown in underlined italics in FIG. 7 is altered by a corresponding mutation, such as a single nucleotide polymorphism, in the corresponding nucleic acid. Stated otherwise, a mutation, such as a substitution mutation or single nucleotide polymorphism, leading to a substitution of at least one of the amino acids at positions 94, 105, 153, 155, 191, 251, 276, 277, 285, 310, 313, 342, 344, 441, 446, and 449 of the wild-type human Tph2 enzyme with a different amino acid indicates a subject having such a substitution is afflicted with or at risk of a serotonergic neurotransmission dysregulation disorder.

Table 4 provides a summary of those mutations (shown in underlined italics) in PAH. In the table, IVS10-11G4A highlighted in underlined bold is an alternatively spliced mutant. This is a mutation in intron which causes a severe form of PKU and is the second frequently reported PKU (R408W in PAH is the most common mutation in PKU and the R is conserved in TPH2). Thus, mutations in the intron(s) of TPH2 cause alternative splicing and give rise to change-of-function mutant(s) indicative of serotonergic neurotransmission dysregulation disorder as described herein.

TABLE 4

Genotype-Phenotype Correlations and Predicted Structural Effect of the Mutations in PAH

| Mutation name-trivial (systematic) | Genotypes[a] | Phenotypes[a] | Structural localization[c] | Structural prediction[b] | Effect |
|---|---|---|---|---|---|
| D59Y (c.175G4T) | D59Y/A403V | HPA | RD; loop a1/b2 | No effect | Folding/regulatory? |
| I65T (c.194T4C) | I65T/I65T | Mild | RD; b2 | Structural | Folding/regulatory? |
|  | I65T/null | Classic/moderate/mild |  |  |  |
| E76G (c.227A4G) | E76G/P122Q | HPA | RD; b3 | Structural | Folding/regulatory? |
| P122Q (c.365C4A) | P122Q/E76G | Mild | CD; loop RDb5/CDa1 | Structural | Folding |
|  | P122Q/F39L | HPA |  |  |  |
| R158Q (c.473G4A) | R158Q/R158Q | Classic | CD; a2 | Structural | Folding |
|  | R158Q/null | Mild |  |  |  |
| G218V (c.653G4T) | G218V/A403V | HPA | CD; loop a4/a5 | No eject | Folding |
|  | G218V/Y414C | Mild |  |  |  |
| R243Q (c.728G4A) | R243Q/null | Mild | CD; b1 | Structural | Folding |
| P244L (c.731C4T) | P244L/I65T | Mild | CD; b1 | Structural | Folding/affinity for cofactor? |
| R252W (c.754C4T) | R252W/R252W | Classic | CD; a6 | Structural | Folding |
| R261Q (c.782G4A) | R261Q/R261Q | Classic/mild | CD; loop a6/b2 | Structural | Folding |
|  | R261Q/null | Classic/moderate/mild |  |  |  |
| Y277D (c.829T4G) | Y277D/Y277D | Classic | CD; b2/a7A | Active site | Catalytic |
| E280K (c.838G4A) | E280K/E280K | Moderate | CD; b2/a7A | Active site | Catalytic/folding |
|  | E280K/null | Classic |  |  |  |
| A309V (c.926C4T) | A309V/A309V | Moderate | CD; a8 | Structural | Folding/affinity for cofactor? |
|  | A309V/null | Classic |  |  |  |
| L311P (c.932T4C) | L311P/L311P | nd (untreated patient) | CD; loop a8/a9 | Structural | Folding |
| IVS10-11G4A (1066-11G4A) | IVS10-11G4A/IVS10-11G4A | Classic/moderate | CD; a11 | nd | Folding |
| R408Q (c.1223G4A) | R408Q/R408Q | HPA | CD; loop a13/b7 | Structural | Folding |
|  | R408Q/null | Mild |  |  |  |
| R408W (c.1222C4T) | R408W/R408W | Classic | CD; loop a13/b7 | Structural | Folding |
| Y414C (c.1241A4G) | Y414C/Y414C | Mild/HPA | CD; b7 | Structural | Folding |

[a]Genotypes and phenotypes in homozygous and functionally hemyzygous (the second mutation is a "null" allele) patients, except for mutations only found in heterozygous patients. Patients referred in PAHdb, Desviat et al. [1999] or Desviat et al. [1997].
[b]According to Erlandsen and Stevens [1999] and Jennings et al. [2000].
[c]RD, regulatory domain; CD, catalytic domain.
Classic: severe PKU
HPA: hyperphenylalaninemia
(cited from Pey et al. Human Mutation 21, 370-378 (2003))

EXAMPLE 3

Identification of R441H and W153R Mutations as Functional SNPs in Human TPH2

This example demonstrates the identification of two mutations, R441H and W153R, as functional SNPs in human TPH2 as predicted based on PAH homology described in Example 2. This example shows R441H in detail; WI53R is identified in essentially the same manner.

Figure 8C:
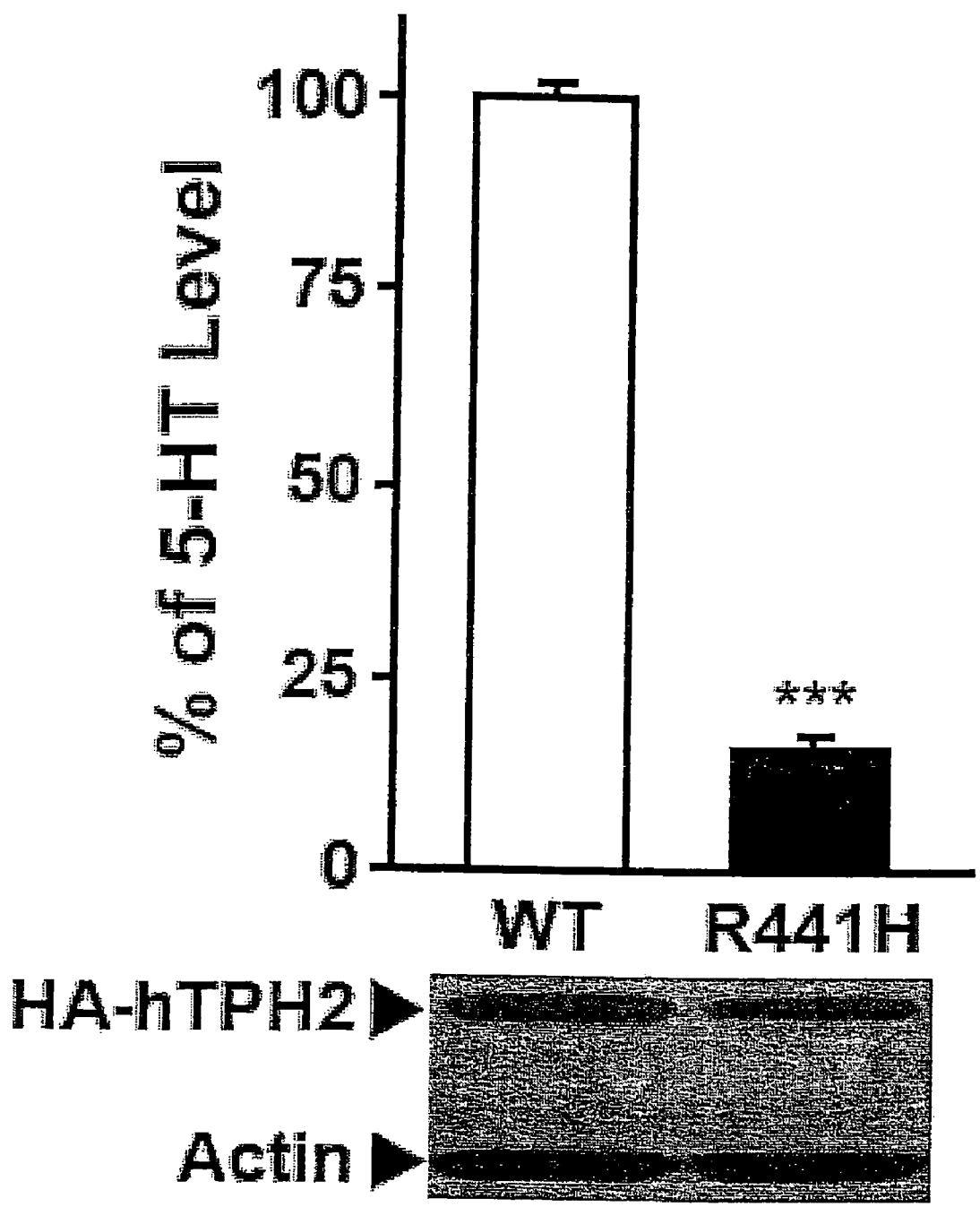
FIG. 8 shows the location of the R441H mutant in human TPH2. A: SEQ ID NO: 21; SEQ ID NO: 22. B: SEQ ID NO: 3; SEQ ID NO: 4; SEQ ID NO: 5; SEQ ID NO: 6; SEQ ID NO: 7; SEQ ID NO: 8; SEQ ID NO: 9; SEQ ID NO: 10; SEQ ID NO: 11; SEQ ID NO: 12; SEQ ID NO: 13; SEQ ID NO: 14.

FIG. 8 shows the location of the R441H mutant (CGT to CAT mutation) and that the Arg is highly conserved by sequence alignment among tyrosine hydroxylase (TH), phenylalanine hydroxylase (PAH), TPH1 and TPH2 in human (h), mouse (m) and rat (r), which belong to a superfamily of aromatic amino acid hydroxylases. Moreover, when R441H was expressed in PC12 cells, the level of serotonin was reduced more than 80% as compared to wild-type. Note that the similar Arg mutation in PAH (R408W) represents the most common (~10%) and the most severe form of phenylketonuria (PKU), consistent with Example 2 above.

Figure 9:
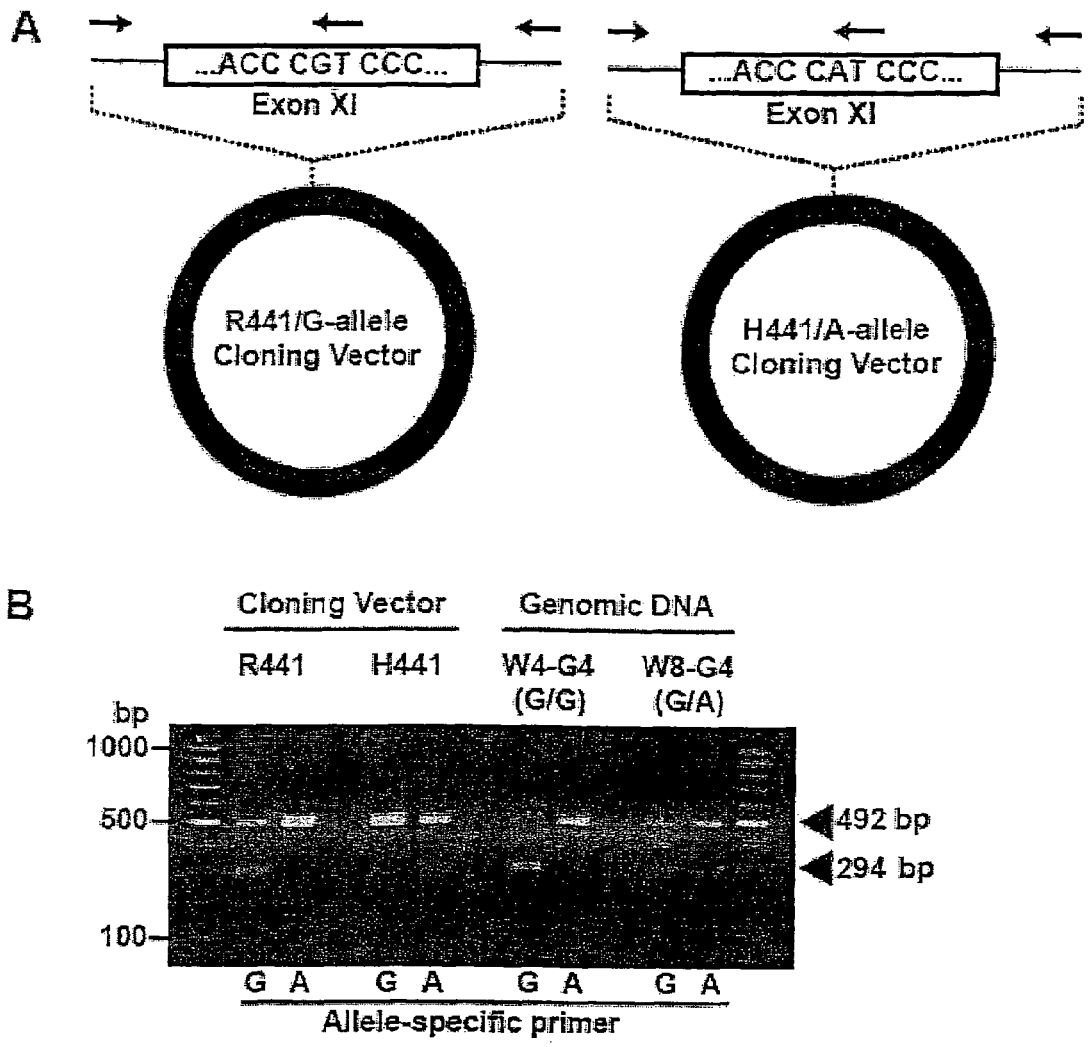
FIG. 9 explains the PCR screening method for R441H mutant (SEQ ID NO: 21; SEQ ID NO: 22).

FIG. 9 explains the PCR screening method for R441 H mutant. The fragment of genomic DNA containing the mutation was also cloned into a cloning vector to confirm the specificity of this method (FIG. 9a).

The PCR reaction consists of two Outer primers and either one of the allele-specific primers. The Outer primers (black arrows) serve as positive control and the allele-specific primer (red arrow) is to identify the SNP in human genomic DNA.

As shown in FIG. 9b, the G allele-specific primer only recognized and amplified in the presence of R441/G allele-containing cloning vector. Similarly, the A allele-specific primer showed its specificity. When human genomic DNA was applied, the wild-type sample W4-G4 (R441/R441, G/G) was only amplified by G allele-specific primer and the heterozygous sample W8-G4 (R441/H441, G/A) exhibited two allele specific PCR fragments.

The specific primers are as follows:

```
R441H primers:
hOuterR441H-F   5'-ATGTGTGAAAGCCTTTGACCCAAAGACA
                (SEQ ID NO: 31)

hOuterR441H-R   5'-TGCGTTATATGACATTGACTGAACTGCT
                (SEQ ID NO: 32)

h441R-G allele  5'-TAGGGATTGAAGTATACTGAGAAGGCAC
                (SEQ ID NO: 33)

h441H-A allele  5'-TAGGGATTGAAGTATACTGAGAAGGCAT
                (SEQ ID NO: 34)

W153R primers:
hOuterW153R-F   5'-TCCAGGAAATCTCGGCGAAGAAGTTCTGA
                (SEQ ID NO: 35)

hOuterW153R-R   5'-AGCATTGCAGCACAGAACATGGCACAGT
                (SEQ ID NO: 36)

h153W-T allele  5'-TGTTTTCAACAGAGCTAGAGGATGTGCACT
                (SEQ ID NO: 37)

h153R-A allele  5'-TGTTTTCAACAGAGCTAGAGGATGTGCACA
                (SEQ ID NO: 38)
```

EXAMPLE 4

Identification of Additional Mutations in Human Tph2

As noted above, functional mutations in human Tph2 can be identified by first identifying mutations in human PAH, and then identifying the corresponding homologous region in human Tph2. A mutation in the corresponding homologous region of human Tph2 is expected to be a functional mutation of Tph2 according to the present invention. Examples of PAH mutations and the corresponding Tph2 mutation are shown in Table 5 below.

TABLE 5

| PAH mutation | Corresponding TPH2 mutation |
|---|---|
| I65T | I94 |
| E76G | E105 |
| W120 stop codon | W153 (W153R) |
| P122Q | P155 |
| R158Q | R191 |
| G218V | G251 |
| R243Q | R276 |
| P244L | P277 |
| R252W | R285 |
| R261Q | Y310 |
| Y277D | E313 |
| E280K | A342 |
| L311P | L344 |
| R408W/R408Q | R441 (R441H) |
| Y414C | Y446 |
|  | P449 (P449R) |

Where a specific amino acid is not given in Table 5, then a mutation inducing any change in the normal sequence (the amino acid to the left of the number identifying the amino acid location) is within the scope of the present invention (for example, a change of: I to T; E to G, P to Q; R to Q; G to V; P to L; R to W; Y to D; E to K; L to P; R to Q; Y to C; R to H; P to R; etc.).

EXAMPLE 5

Identification of Additional Mutations in Human Tph2

Additional examples of mutations useful for carrying out the present invention are the human A65V mutation, the human V66I mutation, the human L175V mutation, and the human Q468X (where X is a stop codon) mutation.

The foregoing is illustrative of the present invention, and is not to be construed as limiting thereof. The invention is defined by the following claims, with equivalents of the claims to be included therein.

The invention claimed is:

1. A method of screening a human subject comprising:
   detecting the presence or absence of a mutation in at least one allele of a Tph2 gene of said human subject;
   wherein said mutation encodes a change in an amino acid of the encoded Tph2 protein of SEQ ID NO: 20;
   wherein said change in an amino acid is R441H; and
   wherein said subject has unipolar major depression.

2. The method of claim 1, wherein said detecting step is carried out by genotyping.

3. The method of claim 1, wherein said detecting step includes a nucleic acid amplification step.

4. The method of claim 1, wherein said detecting step includes an oligonucleotide probe hybridization step.

* * * * *

SEQUENCE LISTING

<160> NUMBER OF SEQ ID NOS: 38

<210> SEQ ID NO 1
<211> LENGTH: 21
<212> TYPE: DNA
<213> ORGANISM: Mus musculus

<400> SEQUENCE: 1

```
tacttcaacc cctacacgca g                                              21
```

<210> SEQ ID NO 2
<211> LENGTH: 21
<212> TYPE: DNA
<213> ORGANISM: Mus musculus

<400> SEQUENCE: 2

```
tacttcaacc gctacacgca g                                              21
```

<210> SEQ ID NO 3
<211> LENGTH: 53
<212> TYPE: PRT
<213> ORGANISM: Homo sapiens

<400> SEQUENCE: 3

```
Arg Ser Tyr Ala Ser Arg Ile Gln Arg Pro Phe Ser Val Lys Phe Asp
 1               5                  10                  15
Pro Tyr Thr Leu Ala Ile Asp Val Leu Asp Ser Pro Gln Ala Val Arg
            20                  25                  30
Arg Ser Leu Glu Gly Val Gln Asp Glu Leu Asp Thr Leu Ala His Ala
        35                  40                  45
Leu Ser Ala Ile Gly
    50
```

<210> SEQ ID NO 4
<211> LENGTH: 53
<212> TYPE: PRT
<213> ORGANISM: Mus musculus

<400> SEQUENCE: 4

```
Arg Asn Tyr Ala Ser Arg Ile Gln Arg Pro Phe Ser Val Lys Phe Asp
 1               5                  10                  15
Pro Tyr Thr Leu Ala Ile Asp Val Leu Asp Ser Pro His Thr Ile Arg
            20                  25                  30
Arg Ser Leu Glu Gly Val Gln Asp Glu Leu His Thr Leu Thr Gln Ala
        35                  40                  45
Leu Ser Ala Ile Ser
    50
```

<210> SEQ ID NO 5
<211> LENGTH: 53
<212> TYPE: PRT
<213> ORGANISM: Rattus norvegicus

<400> SEQUENCE: 5

```
Arg Asn Tyr Ala Ser Arg Ile Gln Arg Pro Phe Ser Val Lys Phe Asp
 1               5                  10                  15
Pro Tyr Thr Leu Ala Ile Asp Val Leu Asp Ser Pro His Thr Ile Gln
            20                  25                  30
Arg Ser Leu Glu Gly Val Gln Asp Glu Leu His Thr Leu Ala His Ala
        35                  40                  45
Leu Ser Ala Ile Ser
    50
```

<210> SEQ ID NO 6
<211> LENGTH: 53
<212> TYPE: PRT
<213> ORGANISM: Homo sapiens

<400> SEQUENCE: 6

Arg Asn Phe Ala Ala Thr Ile Pro Arg Pro Phe Ser Val Arg Tyr Asp
1               5                   10                  15

Pro Tyr Thr Gln Arg Ile Glu Val Leu Asp Asn Thr Gln Gln Leu Lys
            20                  25                  30

Ile Leu Ala Asp Ser Ile Asn Ser Glu Ile Gly Ile Leu Cys Ser Ala
        35                  40                  45

Leu Gln Lys Ile Lys
    50

<210> SEQ ID NO 7
<211> LENGTH: 54
<212> TYPE: PRT
<213> ORGANISM: Mus musculus

<400> SEQUENCE: 7

Arg Thr Phe Ala Ala Thr Ile Pro Arg Pro Phe Ser Val Arg Tyr Asp
1               5                   10                  15

Pro Tyr Thr Gln Arg Val Glu Val Leu Asp Asn Thr Gln Gln Leu Lys
            20                  25                  30

Asn Leu Ala Asp Ser Ile Asn Ser Glu Val Gly Ile Leu Cys His Ala
        35                  40                  45

Leu Gln Lys Ile Lys Ser
    50

<210> SEQ ID NO 8
<211> LENGTH: 54
<212> TYPE: PRT
<213> ORGANISM: Rattus norvegicus

<400> SEQUENCE: 8

Arg Thr Phe Ala Ala Thr Ile Pro Arg Pro Phe Ser Val Arg Tyr Asp
1               5                   10                  15

Pro Tyr Thr Gln Arg Val Glu Val Leu Asp Asn Thr Gln Gln Leu Lys
            20                  25                  30

Ile Leu Ala Asp Ser Ile Asn Ser Glu Val Gly Ile Leu Cys Asn Ala
        35                  40                  45

Leu Gln Lys Ile Lys Ser
    50

<210> SEQ ID NO 9
<211> LENGTH: 58
<212> TYPE: PRT
<213> ORGANISM: Homo sapiens

<400> SEQUENCE: 9

Arg Glu Phe Thr Lys Thr Ile Lys Arg Pro Phe Gly Val Lys Tyr Asn
1               5                   10                  15

Pro Tyr Thr Arg Ser Ile Gln Ile Leu Lys Asp Thr Lys Ser Ile Thr
            20                  25                  30

Ser Ala Met Asn Glu Leu Gln His Asp Leu Asp Val Val Ser Asp Ala
        35                  40                  45

Leu Ala Lys Val Ser Arg Lys Pro Ser Ile
    50                  55

<210> SEQ ID NO 10
<211> LENGTH: 58
<212> TYPE: PRT
<213> ORGANISM: Mus musculus

<400> SEQUENCE: 10

Arg Glu Phe Ala Lys Thr Val Lys Arg Pro Phe Gly Leu Lys Tyr Asn
1               5                   10                  15

Pro Tyr Thr Gln Ser Val Gln Val Leu Arg Asp Thr Lys Ser Ile Thr
            20                  25                  30

Ser Ala Met Asn Glu Leu Arg Tyr Asp Leu Asp Val Ile Ser Asp Ala
        35                  40                  45

Leu Ala Arg Val Thr Arg Trp Pro Ser Val
    50                  55

<210> SEQ ID NO 11
<211> LENGTH: 58
<212> TYPE: PRT
<213> ORGANISM: Rattus norvegicus

<400> SEQUENCE: 11

Arg Glu Phe Ala Lys Thr Val Lys Arg Pro Phe Gly Val Lys Tyr Asn
1               5                   10                  15

Pro Tyr Thr Gln Ser Ile Gln Val Leu Arg Asp Ser Lys Ser Ile Thr
            20                  25                  30

Ser Ala Met Asn Glu Leu Arg His Asp Leu Asp Val Val Asn Asp Ala
        35                  40                  45

Leu Ala Arg Val Ser Arg Trp Pro Ser Val
    50                  55

<210> SEQ ID NO 12
<211> LENGTH: 58
<212> TYPE: PRT
<213> ORGANISM: Homo sapiens

<400> SEQUENCE: 12

Arg Asp Phe Ala Lys Ser Ile Thr Arg Pro Phe Ser Val Tyr Phe Asn
1               5                   10                  15

Pro Tyr Thr Gln Ser Ile Glu Ile Leu Lys Asp Thr Arg Ser Ile Glu
            20                  25                  30

Asn Val Val Gln Asp Leu Arg Ser Asp Leu Asn Thr Val Cys Asp Ala
        35                  40                  45

Leu Asn Lys Met Asn Gln Tyr Leu Gly Ile
    50                  55

<210> SEQ ID NO 13
<211> LENGTH: 58
<212> TYPE: PRT
<213> ORGANISM: Mus musculus

<400> SEQUENCE: 13

Arg Asp Phe Ala Lys Ser Ile Thr Arg Pro Phe Ser Val Tyr Phe Asn
1               5                   10                  15

Arg Tyr Thr Gln Ser Ile Glu Ile Leu Lys Asp Thr Arg Ser Ile Glu
            20                  25                  30

Asn Val Val Gln Asp Leu Arg Ser Asp Leu Asn Thr Val Cys Asp Ala
        35                  40                  45

Leu Asn Lys Met Asn Gln Tyr Leu Gly Ile
    50                  55

<210> SEQ ID NO 14
<211> LENGTH: 58
<212> TYPE: PRT
<213> ORGANISM: Rattus norvegicus

<400> SEQUENCE: 14

Arg Asp Phe Ala Lys Ser Ile Thr Arg Pro Phe Ser Val Tyr Phe Asn
1               5                   10                  15

Pro Tyr Thr Gln Ser Ile Glu Ile Leu Lys Asp Thr Arg Ser Ile Glu
            20                  25                  30

Asn Val Val Gln Asp Leu Arg Ser Asp Leu Asn Thr Val Cys Asp Ala
        35                  40                  45

Leu Asn Lys Met Asn Gln Tyr Leu Gly Ile
        50                  55

<210> SEQ ID NO 15
<211> LENGTH: 134
<212> TYPE: DNA
<213> ORGANISM: Mus musculus

<400> SEQUENCE: 15
catgctcttt ccgacaaggc gtgtgtgaaa tcctttgacc caaagacgac ctgcttgcag    60
gaatgcctaa tcaccacctt tcaggacgct tactttgttt cggacagttt tgaagaagcc   120
aaagaaaaga tgag                                                     134

<210> SEQ ID NO 16
<211> LENGTH: 141
<212> TYPE: DNA
<213> ORGANISM: Mus musculus

<400> SEQUENCE: 16
gtaaacctgc ttttcttcct tctatagaga aagtcacttt taaatgtctc tcgctgttcc    60
ttctgtctaa ctgttttttg tacccgtggc ggttgattgt gttttccttt tgttttttt   120 ttgtttattc tacagggact t                                             141

<210> SEQ ID NO 17
<211> LENGTH: 169
<212> TYPE: DNA
<213> ORGANISM: Mus musculus

<400> SEQUENCE: 17
tgcaaagtca attacccgtc ccttctcggt atacttcaac cgctacacgc agagcattga    60
aattctgaaa gacaccagaa gtattgagaa tgtggtgcag acctgcgca gtgatttgaa    120 cacagtgtgt gatgccttga ataaaatgaa ccaatatctg gggatttga               169

<210> SEQ ID NO 18
<211> LENGTH: 140
<212> TYPE: DNA
<213> ORGANISM: Mus musculus

<400> SEQUENCE: 18
tgcctagaac cagagttatt gtcagcatga gctcttgggg ggtgtagcaa caatgcagtc    60
aatgttatcc aacatcaaca actttctgtg tcatggttgg ctagtaagca tgcaattctg   120
tatgtccata cctctgtgta                                               140

<210> SEQ ID NO 19
<211> LENGTH: 452
<212> TYPE: PRT
<213> ORGANISM: Homo sapiens

<400> SEQUENCE: 19

-continued

```
Met Ser Thr Ala Val Leu Glu Asn Pro Gly Leu Gly Arg Lys Leu Ser
1               5                  10                 15

Asp Phe Gly Gln Glu Thr Ser Tyr Ile Glu Asp Asn Cys Asn Gln Asn
                20                 25                 30

Gly Ala Ile Ser Leu Ile Phe Ser Leu Lys Glu Glu Val Gly Ala Leu
            35                 40                 45

Ala Lys Val Leu Arg Leu Phe Glu Glu Asn Asp Val Asn Leu Thr His
    50                 55                 60

Ile Glu Ser Arg Pro Ser Arg Leu Lys Lys Asp Glu Tyr Glu Phe Phe
65                 70                 75                 80

Thr His Leu Asp Lys Arg Ser Leu Pro Ala Leu Thr Asn Ile Ile Lys
                85                 90                 95

Ile Leu Arg His Asp Ile Gly Ala Thr Val His Glu Leu Ser Arg Asp
            100                105                110

Lys Lys Lys Asp Thr Val Pro Trp Phe Pro Arg Thr Ile Gln Glu Leu
    115                120                125

Asp Arg Phe Ala Asn Gln Ile Leu Ser Tyr Gly Ala Glu Leu Asp Ala
130                135                140

Asp His Pro Gly Phe Lys Asp Pro Val Tyr Arg Ala Arg Arg Lys Gln
145                150                155                160

Phe Ala Asp Ile Ala Tyr Asn Tyr Arg His Gly Gln Pro Ile Pro Arg
                165                170                175

Val Glu Tyr Met Glu Glu Lys Lys Thr Trp Gly Thr Val Phe Lys
            180                185                190

Thr Leu Lys Ser Leu Tyr Lys Thr His Ala Cys Tyr Glu Tyr Asn His
            195                200                205

Ile Phe Pro Leu Leu Glu Lys Tyr Cys Gly Phe His Glu Asp Asn Ile
    210                215                220

Pro Gln Leu Glu Asp Val Ser Gln Phe Leu Gln Thr Cys Thr Gly Phe
225                230                235                240

Arg Leu Arg Pro Val Ala Gly Leu Leu Ser Arg Asp Phe Leu Gly
                245                250                255

Gly Leu Ala Phe Arg Val Phe His Cys Thr Gln Tyr Ile Arg His Gly
            260                265                270

Ser Lys Pro Met Tyr Thr Pro Glu Pro Asp Ile Cys His Glu Leu Leu
    275                280                285

Gly His Val Pro Leu Phe Ser Asp Arg Ser Phe Ala Gln Phe Ser Gln
    290                295                300

Glu Ile Gly Leu Ala Ser Leu Gly Ala Pro Asp Glu Tyr Ile Glu Lys
305                310                315                320

Leu Ala Thr Ile Tyr Trp Phe Thr Val Glu Phe Gly Leu Cys Lys Gln
                325                330                335

Gly Asp Ser Ile Lys Ala Tyr Gly Ala Gly Leu Leu Ser Ser Phe Gly
            340                345                350

Glu Leu Gln Tyr Cys Leu Ser Glu Lys Pro Lys Leu Leu Pro Leu Glu
        355                360                365

Leu Glu Lys Thr Ala Ile Gln Asn Tyr Thr Val Thr Glu Phe Gln Pro
    370                375                380

Leu Tyr Tyr Val Ala Glu Ser Phe Asn Asp Ala Lys Glu Lys Val Arg
385                390                395                400

Asn Phe Ala Ala Thr Ile Pro Arg Pro Phe Ser Val Arg Tyr Asp Pro
                405                410                415

Tyr Thr Gln Arg Ile Glu Val Leu Asp Asn Thr Gln Gln Leu Lys Ile
```

-continued

```
                    420                 425                 430
Leu Ala Asp Ser Ile Asn Ser Glu Ile Gly Ile Leu Cys Ser Ala Leu
                435                 440                 445
Gln Lys Ile Lys
    450

<210> SEQ ID NO 20
<211> LENGTH: 490
<212> TYPE: PRT
<213> ORGANISM: Homo sapiens

<400> SEQUENCE: 20

Met Gln Pro Ala Met Met Met Phe Ser Ser Lys Tyr Trp Ala Arg Arg
1               5                   10                  15
Gly Phe Ser Leu Asp Ser Ala Val Pro Glu Glu His Gln Leu Leu Gly
                20                  25                  30
Ser Ser Thr Leu Asn Lys Pro Asn Ser Gly Lys Asn Asp Asp Lys Gly
            35                  40                  45
Asn Lys Gly Ser Ser Lys Arg Glu Ala Ala Thr Glu Ser Gly Lys Thr
    50                  55                  60
Ala Val Val Phe Ser Leu Lys Asn Glu Val Gly Gly Leu Val Lys Ala
65                  70                  75                  80
Leu Arg Leu Phe Gln Glu Lys Arg Val Asn Met Val His Ile Glu Ser
                85                  90                  95
Arg Lys Ser Arg Arg Arg Ser Ser Glu Val Glu Ile Phe Val Asp Cys
            100                 105                 110
Glu Cys Gly Lys Thr Glu Phe Asn Glu Leu Ile Gln Leu Leu Lys Phe
        115                 120                 125
Gln Thr Thr Ile Val Thr Leu Asn Pro Pro Glu Asn Ile Trp Thr Glu
    130                 135                 140
Glu Glu Glu Leu Glu Asp Val Pro Trp Phe Pro Arg Lys Ile Ser Glu
145                 150                 155                 160
Leu Asp Lys Cys Ser His Arg Val Leu Met Tyr Gly Ser Glu Leu Asp
                165                 170                 175
Ala Asp His Pro Gly Phe Lys Asp Asn Val Tyr Arg Gln Arg Arg Lys
            180                 185                 190
Tyr Phe Val Asp Val Ala Met Gly Tyr Lys Tyr Gly Gln Pro Ile Pro
        195                 200                 205
Arg Val Glu Tyr Thr Glu Glu Thr Lys Thr Trp Gly Val Val Phe
    210                 215                 220
Arg Glu Leu Ser Lys Leu Tyr Pro Thr His Ala Cys Arg Glu Tyr Leu
225                 230                 235                 240
Lys Asn Phe Pro Leu Leu Thr Lys Tyr Cys Gly Tyr Arg Glu Asp Asn
                245                 250                 255
Val Pro Gln Leu Glu Asp Val Ser Met Phe Leu Lys Glu Arg Ser Gly
            260                 265                 270
Phe Thr Val Arg Pro Val Ala Gly Tyr Leu Ser Pro Arg Asp Phe Leu
        275                 280                 285
Ala Gly Leu Ala Tyr Arg Val Phe His Cys Thr Gln Tyr Ile Arg His
    290                 295                 300
Gly Ser Asp Pro Leu Tyr Thr Pro Glu Pro Asp Thr Cys His Glu Leu
305                 310                 315                 320
Leu Gly His Val Pro Leu Leu Ala Asp Pro Lys Phe Ala Gln Phe Ser
                325                 330                 335
```

```
Gln Glu Ile Gly Leu Ala Ser Leu Gly Ala Ser Asp Glu Asp Val Gln
            340                 345                 350
Lys Leu Ala Thr Cys Tyr Phe Phe Thr Ile Glu Phe Gly Leu Cys Lys
        355                 360                 365
Gln Glu Gly Gln Leu Arg Ala Tyr Gly Ala Gly Leu Leu Ser Ser Ile
    370                 375                 380
Gly Glu Leu Lys His Ala Leu Ser Asp Lys Ala Cys Val Lys Ala Phe
385                 390                 395                 400
Asp Pro Lys Thr Thr Cys Leu Gln Glu Cys Leu Ile Thr Thr Phe Gln
                405                 410                 415
Glu Ala Tyr Phe Val Ser Glu Ser Phe Glu Glu Ala Lys Glu Lys Met
            420                 425                 430
Arg Asp Phe Ala Lys Ser Ile Thr Arg Pro Phe Ser Val Tyr Phe Asn
        435                 440                 445
Pro Tyr Thr Gln Ser Ile Glu Ile Leu Lys Asp Thr Arg Ser Ile Glu
    450                 455                 460
Asn Val Val Gln Asp Leu Arg Ser Asp Leu Asn Thr Val Cys Asp Ala
465                 470                 475                 480
Leu Asn Lys Met Asn Gln Tyr Leu Gly Ile
                485                 490

<210> SEQ ID NO 21
<211> LENGTH: 21
<212> TYPE: DNA
<213> ORGANISM: Homo sapiens

<400> SEQUENCE: 21
tcaattaccc gtcccttctc a                                           21

<210> SEQ ID NO 22
<211> LENGTH: 21
<212> TYPE: DNA
<213> ORGANISM: Homo sapiens

<400> SEQUENCE: 22
tcaattaccc atcccttctc a                                           21

<210> SEQ ID NO 23
<211> LENGTH: 196
<212> TYPE: DNA
<213> ORGANISM: Homo sapiens

<400> SEQUENCE: 23
ggtcagccca ttcccagggt ggagtatact gaagaagaaa ctaaaacttg gggtgttgta    60
ttccgggagc tctccaaact ctatcccact catgcttgcc gagagtattt gaaaaacttc   120
cctctgctga ctaaatactg tggctacaga gaggacaatg tgcctcaact cgaagatgtc   180
tccatgtttc tgaaag                                                  196

<210> SEQ ID NO 24
<211> LENGTH: 360
<212> TYPE: DNA
<213> ORGANISM: Homo sapiens

<400> SEQUENCE: 24
gtaagatttc acacaggctg tctcttatta gtcaatatcc tcaattgcct tccaaggaca    60
caggttgcag caatggctct ttttccaaaa aaggaaaaac agtgattaa aaaattgttg   120 gctttgagcc aacaattacc tgcggccacc tgtgggaagc agagcaaggg actcagctgc   180
```

-continued

```
ttttgcagct caggagcttg ctgaggcctc tttgtggctg gttgttgtaa atggtaaggc    240
ccaaaggata tttgcaagtt cagctctgag cttttctga tccaggagct gctgtgctgg     300
gctacatgag tatgaaatga cctccaaaag tgccttttta tttgctttgt taaaagtat     360
```

<210> SEQ ID NO 25
<211> LENGTH: 28
<212> TYPE: DNA
<213> ORGANISM: Artificial
<220> FEATURE:
<223> OTHER INFORMATION: Primer

<400> SEQUENCE: 25
accgatatca tgcagcccgc aatgatga                                        28

<210> SEQ ID NO 26
<211> LENGTH: 30
<212> TYPE: DNA
<213> ORGANISM: Artificial
<220> FEATURE:
<223> OTHER INFORMATION: Primer

<400> SEQUENCE: 26
aaatctagat tgctacaccc cccaagagct                                      30

<210> SEQ ID NO 27
<211> LENGTH: 26
<212> TYPE: DNA
<213> ORGANISM: Artificial
<220> FEATURE:
<223> OTHER INFORMATION: Primer

<400> SEQUENCE: 27
tttgacccaa agacgacctg cttgca                                          26

<210> SEQ ID NO 28
<211> LENGTH: 28
<212> TYPE: DNA
<213> ORGANISM: Artificial
<220> FEATURE:
<223> OTHER INFORMATION: Primer

<400> SEQUENCE: 28
tgcatgctta ctagccaacc atgacaca                                        28

<210> SEQ ID NO 29
<211> LENGTH: 26
<212> TYPE: DNA
<213> ORGANISM: Artificial
<220> FEATURE:
<223> OTHER INFORMATION: Primer

<400> SEQUENCE: 29
cagaatttca atgctctgcg tgtggg                                          26

<210> SEQ ID NO 30
<211> LENGTH: 26
<212> TYPE: DNA
<213> ORGANISM: Artificial
<220> FEATURE:
<223> OTHER INFORMATION: Primer

<400> SEQUENCE: 30
cagaatttca atgctctgcg tgtggc                                          26

<210> SEQ ID NO 31
<211> LENGTH: 28
<212> TYPE: DNA
<213> ORGANISM: Artificial
<220> FEATURE:
<223> OTHER INFORMATION: Primer

<400> SEQUENCE: 31
atgtgtgaaa gcctttgacc caaagaca                                      28

<210> SEQ ID NO 32
<211> LENGTH: 28
<212> TYPE: DNA
<213> ORGANISM: Artificial
<220> FEATURE:
<223> OTHER INFORMATION: Primer

<400> SEQUENCE: 32
tgcgttatat gacattgact gaactgct                                      28

<210> SEQ ID NO 33
<211> LENGTH: 28
<212> TYPE: DNA
<213> ORGANISM: Artificial
<220> FEATURE:
<223> OTHER INFORMATION: Primer

<400> SEQUENCE: 33
tagggattga agtatactga gaaggcac                                      28

<210> SEQ ID NO 34
<211> LENGTH: 28
<212> TYPE: DNA
<213> ORGANISM: Artificial
<220> FEATURE:
<223> OTHER INFORMATION: Primer

<400> SEQUENCE: 34
tagggattga agtatactga gaaggcat                                      28

<210> SEQ ID NO 35
<211> LENGTH: 29
<212> TYPE: DNA
<213> ORGANISM: Artificial
<220> FEATURE:
<223> OTHER INFORMATION: Primer

<400> SEQUENCE: 35
tccaggaaat ctcggcgaag aagttctga                                     29

<210> SEQ ID NO 36
<211> LENGTH: 28
<212> TYPE: DNA
<213> ORGANISM: Artificial
<220> FEATURE:
<223> OTHER INFORMATION: Primer

<400> SEQUENCE: 36
agcattgcag cacagaacat ggcacagt                                      28

<210> SEQ ID NO 37
<211> LENGTH: 30
<212> TYPE: DNA
<213> ORGANISM: Artificial
<220> FEATURE:
<223> OTHER INFORMATION: Primer

```
<400> SEQUENCE: 37
tgttttcaac agagctagag gatgtgcact                                      30

<210> SEQ ID NO 38
<211> LENGTH: 30
<212> TYPE: DNA
<213> ORGANISM: Artificial
<220> FEATURE:
<223> OTHER INFORMATION: Primer

<400> SEQUENCE: 38
tgttttcaac agagctagag gatgtgcaca                                      30
```